US012773308B2

(12) United States Patent
Magen et al.

(10) Patent No.: US 12,773,308 B2
(45) Date of Patent: Oct. 27, 2026

(54) SUPPORT RING, AORTIC PROSTHESIS AND METHOD OF FORMING

(71) Applicant: Bolton Medical, Inc., Sunrise, FL (US)

(72) Inventors: Eitan Magen, Sunrise, FL (US); Eduardo Alejandro Garcia, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 937 days.

(21) Appl. No.: 17/868,296

(22) Filed: Jul. 19, 2022

(65) Prior Publication Data

US 2023/0063108 A1 Mar. 2, 2023

Related U.S. Application Data

(63) Continuation of application No. PCT/US2022/033239, filed on Jun. 13, 2022.

(60) Provisional application No. 63/210,265, filed on Jun. 14, 2021, provisional application No. 63/210,271, filed on Jun. 14, 2021.

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01); *A61F 2002/075* (2013.01); *A61F 2210/0014* (2013.01); *A61F 2250/0039* (2013.01); *A61F 2250/0098* (2013.01)

(58) Field of Classification Search
CPC ........ A61F 2220/0025; A61F 2002/061; A61F 2250/0039; A61F 2/07; A61B 2017/00243
USPC .................. 623/2.37; 24/20 S, 334; 606/151
See application file for complete search history.

(56) References Cited

U.S. PATENT DOCUMENTS 4,787,391 A 11/1988 Elefteriades
5,123,917 A 6/1992 Lee
5,242,452 A 9/1993 Inoue
(Continued)

FOREIGN PATENT DOCUMENTS

CN 100562297 C 11/2009
CN 1867302 B 3/2011
(Continued)

OTHER PUBLICATIONS

International Search Report and Written Opinion for Application No. PCT/US2022/033239 Nov. 7, 2022.
(Continued)

*Primary Examiner* — Brian E Pellegrino
(74) *Attorney, Agent, or Firm* — Stephen J. Kenny; Emily H. Yasharpour; Foley Hoag LLP

(57) ABSTRACT

A support ring for an aortic prosthesis includes a helical coil extending in an arc and defining a space between a helical coil first end and helical coil second end in opposing relation to each other. A wire extending through the lumen defined by the helical coil includes a wire first end and a wire second end that are fixed to each other, and a length between the wire first end and the wire second end that traverses the space between helical coil first end and the helical coil second end. A branch sleeve assembly includes a graft sleeve having a proximal end that defines a plane that intersects a plane defined by the distal end of the graft sleeve, and a support ring fixed to the graft sleeve wall that is closer to the proximal end of the graft sleeve than to the graft sleeve distal end.

18 Claims, 11 Drawing Sheets

(56) References Cited

U.S. PATENT DOCUMENTS

| | | | |
|---|---|---|---|
| 5,507,769 A | 4/1996 | Marin et al. | |
| 5,713,948 A | 2/1998 | Uflacker | |
| 5,755,769 A | 5/1998 | Richard et al. | |
| 5,873,906 A | 2/1999 | Lau et al. | |
| 5,984,955 A | 11/1999 | Wisselink | |
| 6,113,623 A | 9/2000 | Sgro | |
| 6,171,334 B1 | 1/2001 | Cox | |
| 6,280,464 B1 | 8/2001 | Hayashi | |
| 6,325,826 B1 | 12/2001 | Vardi et al. | |
| 6,352,561 B1 | 3/2002 | Leopold et al. | |
| 6,395,018 B1 | 5/2002 | Castaneda | |
| 6,610,087 B1 | 8/2003 | Zarbatany et al. | |
| 6,645,242 B1 | 11/2003 | Quinn | |
| 6,776,791 B1 | 8/2004 | Stallings et al. | |
| 7,112,216 B2 | 9/2006 | Gregorich | |
| 7,189,257 B2 | 3/2007 | Schmitt et al. | |
| 7,306,623 B2 | 12/2007 | Watson | |
| 7,326,242 B2 | 2/2008 | Eidenschink | |
| 7,435,253 B1 | 10/2008 | Hartley et al. | |
| 7,637,940 B2 | 12/2009 | Kocur et al. | |
| 7,645,298 B2 | 1/2010 | Hartley et al. | |
| 7,678,141 B2 | 3/2010 | Greenan et al. | |
| 7,763,063 B2 | 7/2010 | Arbefeuille et al. | |
| 7,842,081 B2 | 11/2010 | Yadin | |
| 8,007,605 B2 | 8/2011 | Arbefeuille et al. | |
| 8,062,345 B2 | 11/2011 | Ouellette et al. | |
| 8,062,346 B2 | 11/2011 | Quigley et al. | |
| 8,062,349 B2 | 11/2011 | Moore et al. | |
| 8,070,790 B2 | 12/2011 | Berra et al. | |
| 8,128,686 B2 | 3/2012 | Paul, Jr. et al. | |
| 8,172,895 B2 | 5/2012 | Anderson et al. | |
| 8,236,040 B2 | 8/2012 | Mayberry et al. | |
| 8,277,501 B2 | 10/2012 | Chalekian et al. | |
| 8,292,943 B2 | 10/2012 | Berra et al. | |
| 8,298,278 B2 | 10/2012 | Gregorich et al. | |
| 8,308,790 B2 | 11/2012 | Arbefeuille et al. | |
| 8,333,800 B2 | 12/2012 | Bruszewski et al. | |
| 8,343,211 B2 | 1/2013 | Gregorich et al. | |
| 8,377,113 B2 | 2/2013 | Hartley et al. | |
| 8,449,595 B2 | 5/2013 | Ouellette et al. | |
| 8,470,018 B2 | 6/2013 | Hartley et al. | |
| 8,480,725 B2 | 7/2013 | Rasmussen et al. | |
| 8,480,728 B2 | 7/2013 | Gregorich et al. | |
| 8,486,129 B2 | 7/2013 | Lautherjung | |
| 8,500,792 B2 | 8/2013 | Berra | |
| 8,506,622 B2 | 8/2013 | Bruszewski et al. | |
| 8,540,764 B2 | 9/2013 | Bruszewski et al. | |
| 8,636,788 B2 | 1/2014 | Arbefeuille et al. | |
| 8,641,752 B1 | 2/2014 | Holm et al. | |
| 8,702,786 B2 | 4/2014 | Roeder et al. | |
| 8,728,148 B2 | 5/2014 | Roeder et al. | |
| 8,740,963 B2 | 6/2014 | Arbefeuille et al. | |
| 8,771,336 B2 | 7/2014 | Roeder | |
| 8,795,349 B2 | 8/2014 | Huser et al. | |
| 8,808,351 B2 | 8/2014 | Osborne | |
| 8,828,074 B2 | 9/2014 | Xiao et al. | |
| 8,870,939 B2 | 10/2014 | Roeder et al. | |
| 8,911,491 B2 | 12/2014 | Hanson et al. | |
| 8,915,955 B2 | 12/2014 | West et al. | |
| 8,915,956 B2 | 12/2014 | Schaeffer et al. | |
| 8,926,693 B2 | 1/2015 | Duffy et al. | |
| 9,101,455 B2 | 8/2015 | Roeder et al. | |
| 9,101,456 B2 * | 8/2015 | Hartley | A61F 2/856 623/1.35 |
| 9,101,506 B2 | 8/2015 | Arbefeuille et al. | |
| 9,173,755 B2 | 11/2015 | Berra et al. | |
| 9,198,786 B2 | 12/2015 | Moore et al. | |
| 9,220,617 B2 | 12/2015 | Berra | |
| 9,259,336 B2 | 2/2016 | Schaeffer et al. | |
| 9,320,631 B2 | 4/2016 | Moore et al. | |
| 9,333,104 B2 | 5/2016 | Ouellette et al. | |
| 9,358,142 B2 | 6/2016 | Johnson | |
| 9,364,314 B2 | 6/2016 | Berra et al. | |
| 9,408,734 B2 | 8/2016 | Arbefeuille et al. | |
| 9,408,735 B2 | 8/2016 | Arbefeuille et al. | |
| 9,439,751 B2 | 9/2016 | White et al. | |
| 9,561,124 B2 | 2/2017 | Arbefeuille et al. | |
| 9,592,112 B2 | 3/2017 | Arbefeuille et al. | |
| 9,597,204 B2 | 3/2017 | Benary et al. | |
| 9,655,712 B2 | 5/2017 | Berra et al. | |
| 9,770,322 B2 | 9/2017 | Burkart et al. | |
| 9,827,123 B2 | 11/2017 | Arbefeuille et al. | |
| 9,839,542 B2 | 12/2017 | Bruszewski et al. | |
| 9,861,503 B2 | 1/2018 | Barthold et al. | |
| 9,877,857 B2 | 1/2018 | Arbefeuille et al. | |
| 9,907,680 B2 | 3/2018 | Skender | |
| 9,907,686 B2 | 3/2018 | Ouellette et al. | |
| 9,913,743 B2 | 3/2018 | Arbefeuille et al. | |
| 9,925,080 B2 | 3/2018 | Arbefeuille et al. | |
| 10,004,620 B2 | 6/2018 | Treacy et al. | |
| 10,005,269 B2 | 6/2018 | Hall et al. | |
| 10,080,674 B2 | 9/2018 | Yuan et al. | |
| 10,105,248 B2 | 10/2018 | Berra et al. | |
| 10,105,250 B2 | 10/2018 | Berra | |
| 10,182,930 B2 | 1/2019 | Moore et al. | |
| 10,213,291 B2 | 2/2019 | Berra et al. | |
| 10,245,137 B2 | 4/2019 | Scutti et al. | |
| 10,265,202 B2 | 4/2019 | Greenberg et al. | |
| 10,299,951 B2 | 5/2019 | Arbefeuille et al. | |
| 10,307,275 B2 | 6/2019 | Berra et al. | |
| 10,390,930 B2 | 8/2019 | Arbefeuille et al. | |
| 10,478,320 B2 | 11/2019 | Shahriari | |
| 10,485,684 B2 | 11/2019 | Marmur et al. | |
| 10,512,556 B2 | 12/2019 | Longo et al. | |
| 10,617,542 B2 | 4/2020 | Chakfe et al. | |
| 10,702,406 B2 | 7/2020 | Swift et al. | |
| 10,744,012 B2 | 8/2020 | Bonsignore et al. | |
| 10,898,357 B2 | 1/2021 | Arbefeuille et al. | |
| 10,987,235 B2 | 4/2021 | Eubanks et al. | |
| 10,987,873 B2 | 4/2021 | Moldave et al. | |
| 11,000,359 B2 | 5/2021 | Torrance et al. | |
| 11,219,540 B2 | 1/2022 | Arbefeuille | |
| 11,278,390 B2 | 3/2022 | Lostetter | |
| 11,291,572 B2 | 4/2022 | Garcia | |
| 11,351,025 B2 | 6/2022 | Lostetter | |
| 11,369,466 B2 | 6/2022 | Arbefeuille | |
| 11,399,929 B2 | 8/2022 | Arbefeuille | |
| 11,413,177 B2 | 8/2022 | Lostetter | |
| 11,478,349 B2 | 10/2022 | Torrance et al. | |
| 11,547,584 B2 | 1/2023 | Lostetter | |
| 11,779,454 B2 | 10/2023 | Arbefeuille | |
| 11,801,129 B2 | 10/2023 | Lostetter | |
| 12,048,622 B2 | 7/2024 | Arbefeuille | |
| 12,083,030 B2 | 9/2024 | Lostetter | |
| 12,127,931 B2 | 10/2024 | Lostetter | |
| 12,427,010 B2 | 9/2025 | Arbefeuille | |
| 2002/0038144 A1 | 3/2002 | Trout et al. | |
| 2002/0062133 A1 | 5/2002 | Gilson et al. | |
| 2002/0090725 A1 | 7/2002 | Simpson et al. | |
| 2002/0151956 A1 | 10/2002 | Chobotov et al. | |
| 2002/0177890 A1 | 11/2002 | Lenker | |
| 2002/0188344 A1 | 12/2002 | Bolea et al. | |
| 2002/0193872 A1 | 12/2002 | Trout et al. | |
| 2002/0198585 A1 | 12/2002 | Wisselink | |
| 2004/0059406 A1 | 3/2004 | Cully et al. | |
| 2004/0073289 A1 | 4/2004 | Hartley | |
| 2004/0138737 A1 | 7/2004 | Davidson et al. | |
| 2005/0010240 A1 * | 1/2005 | Mathis | A61F 2/2451 606/151 |
| 2005/0102021 A1 | 5/2005 | Osborne | |
| 2005/0102023 A1 | 5/2005 | Yadin et al. | |
| 2005/0119722 A1 | 6/2005 | Styrc et al. | |
| 2005/0131517 A1 | 6/2005 | Hartley et al. | |
| 2005/0131518 A1 | 6/2005 | Hartley et al. | |
| 2005/0131519 A1 | 6/2005 | Hartley | |
| 2005/0131523 A1 | 6/2005 | Bashiri et al. | |
| 2005/0154444 A1 | 7/2005 | Quadri | |
| 2005/0171597 A1 | 8/2005 | Boatman et al. | |
| 2006/0015171 A1 | 1/2006 | Armstrong | |
| 2006/0020319 A1 | 1/2006 | Kim et al. | |
| 2006/0095118 A1 | 5/2006 | Hartley | |
| 2006/0155359 A1 | 7/2006 | Watson | |
| 2006/0184226 A1 | 8/2006 | Austin | |
| 2006/0247760 A1 | 11/2006 | Ganesan et al. | |

(56) References Cited

U.S. PATENT DOCUMENTS

| | | | |
|---|---|---|---|
| 2006/0247761 A1 | 11/2006 | Greenberg et al. | |
| 2007/0021822 A1 | 1/2007 | Boatman | |
| 2007/0055358 A1 | 3/2007 | Krolik et al. | |
| 2007/0055360 A1 | 3/2007 | Hanson et al. | |
| 2007/0067023 A1 | 3/2007 | Kveen et al. | |
| 2007/0112418 A1 | 5/2007 | Eidenschink et al. | |
| 2007/0135904 A1 | 6/2007 | Eidenschink et al. | |
| 2007/0208414 A1 | 9/2007 | Sorenson et al. | |
| 2007/0208419 A1 | 9/2007 | Meyer et al. | |
| 2007/0213805 A1 | 9/2007 | Schaeffer et al. | |
| 2007/0225797 A1 | 9/2007 | Krivoruhko | |
| 2007/0233223 A1 | 10/2007 | Styrc | |
| 2007/0244542 A1 | 10/2007 | Greenan et al. | |
| 2007/0244547 A1 | 10/2007 | Greenan | |
| 2007/0250152 A1 | 10/2007 | Xiao et al. | |
| 2008/0091260 A1 | 4/2008 | Pomeranz et al. | |
| 2008/0132988 A1 | 6/2008 | Jordan | |
| 2008/0264102 A1 | 10/2008 | Berra | |
| 2008/0281399 A1 | 11/2008 | Hartley et al. | |
| 2009/0030502 A1 | 1/2009 | Sun et al. | |
| 2009/0043377 A1 | 2/2009 | Greenberg et al. | |
| 2009/0048663 A1 | 2/2009 | Greenberg | |
| 2009/0164001 A1 | 6/2009 | Biggs et al. | |
| 2009/0248135 A1 | 10/2009 | Bruszewski et al. | |
| 2009/0264990 A1 | 10/2009 | Bruszewski et al. | |
| 2010/0004730 A1 | 1/2010 | Benjamin et al. | |
| 2010/0030253 A1 | 2/2010 | Harris et al. | |
| 2010/0057186 A1 | 3/2010 | West et al. | |
| 2010/0063576 A1 | 3/2010 | Schaeffer et al. | |
| 2010/0121429 A1 | 5/2010 | Greenan et al. | |
| 2010/0268319 A1 | 10/2010 | Bruszewski et al. | |
| 2010/0312326 A1 | 12/2010 | Chuter et al. | |
| 2010/0316830 A1 | 12/2010 | Hartley et al. | |
| 2011/0077730 A1 | 3/2011 | Fenster | |
| 2011/0190862 A1 | 8/2011 | Bashiri et al. | |
| 2011/0190868 A1 | 8/2011 | Ducke et al. | |
| 2011/0257720 A1 | 10/2011 | Peterson et al. | |
| 2011/0319983 A1 | 12/2011 | Zhu et al. | |
| 2012/0022630 A1 | 1/2012 | Wubbeling | |
| 2012/0035714 A1 | 2/2012 | Ducke et al. | |
| 2012/0172965 A1 | 7/2012 | Kratzberg et al. | |
| 2012/0191174 A1 | 7/2012 | Vinluan et al. | |
| 2012/0221096 A1 | 8/2012 | Roeder et al. | |
| 2012/0296360 A1 | 11/2012 | Norris et al. | |
| 2013/0116773 A1 | 5/2013 | Roeder et al. | |
| 2013/0116775 A1 | 5/2013 | Roeder et al. | |
| 2013/0123900 A1 | 5/2013 | Eblacas et al. | |
| 2013/0158648 A1 | 6/2013 | Hartley et al. | |
| 2013/0211505 A1 | 8/2013 | Robison | |
| 2013/0282102 A1 | 10/2013 | Peterson | |
| 2013/0289696 A1 | 10/2013 | Maggard et al. | |
| 2013/0289713 A1 | 10/2013 | Pearson et al. | |
| 2014/0046428 A1 | 2/2014 | Cragg et al. | |
| 2014/0180378 A1 | 6/2014 | Roeder | |
| 2014/0200651 A1 | 7/2014 | Chuter et al. | |
| 2014/0249615 A1 | 9/2014 | Schreck et al. | |
| 2014/0324150 A1 | 10/2014 | Stephens et al. | |
| 2015/0105819 A1 | 4/2015 | Becking et al. | |
| 2015/0105849 A1 | 4/2015 | Cohen et al. | |
| 2015/0105850 A1 | 4/2015 | Shahriari | |
| 2015/0202065 A1 | 7/2015 | Shalev et al. | |
| 2015/0202067 A1 | 7/2015 | Barrand et al. | |
| 2015/0216686 A1 | 8/2015 | Chakfe et al. | |
| 2015/0335452 A1 | 11/2015 | Rao et al. | |
| 2016/0100969 A1 | 4/2016 | Lesmeister et al. | |
| 2016/0106564 A1 | 4/2016 | Roeder et al. | |
| 2016/0120667 A1 | 5/2016 | Bolduc et al. | |
| 2016/0184078 A1 | 6/2016 | Choubey et al. | |
| 2016/0199207 A1 | 7/2016 | Treacy et al. | |
| 2016/0296353 A1 | 10/2016 | Skender | |
| 2016/0302950 A1 | 10/2016 | Marmur et al. | |
| 2017/0281382 A1 | 10/2017 | Lostetter et al. | |
| 2018/0153680 A1 | 6/2018 | Greenberg et al. | |
| 2018/0200089 A1* | 7/2018 | Eller | A61F 2/07<br>623/1.35 |
| 2019/0159886 A1 | 5/2019 | Antonio Lourenco | |
| 2019/0231514 A1 | 8/2019 | Arbefeuille | |
| 2019/0231571 A1 | 8/2019 | Lostetter | |
| 2019/0247178 A1 | 8/2019 | Arbefeuille | |
| 2019/0247213 A1 | 8/2019 | Lostetter | |
| 2019/0269497 A1 | 9/2019 | Arbefeuille | |
| 2019/0269498 A1 | 9/2019 | Arbefeuille et al. | |
| 2019/0282355 A1 | 9/2019 | Lostetter | |
| 2019/0328556 A1 | 10/2019 | Eubanks et al. | |
| 2019/0350694 A1 | 11/2019 | Arbefeuille et al. | |
| 2020/0246165 A1 | 8/2020 | Arbefeuille et al. | |
| 2020/0352700 A1 | 11/2020 | Torrance et al. | |
| 2021/0052364 A1 | 2/2021 | Guo et al. | |
| 2021/0100669 A1 | 4/2021 | Arbefeuille et al. | |
| 2021/0236262 A1 | 8/2021 | Torrance et al. | |
| 2022/0087841 A1 | 3/2022 | Arbefeuille | |
| 2022/0168091 A1 | 6/2022 | Lostetter | |
| 2022/0257361 A1 | 8/2022 | Lostetter | |
| 2022/0304798 A1 | 9/2022 | Arbefeuille | |
| 2022/0313419 A1 | 10/2022 | Arbefeuille | |
| 2022/0378594 A1 | 12/2022 | Lostetter | |
| 2022/0395365 A1 | 12/2022 | Lostetter et al. | |
| 2023/0063108 A1 | 3/2023 | Magen et al. | |
| 2024/0058114 A1 | 2/2024 | Arbefeuille | |

FOREIGN PATENT DOCUMENTS

| | | | |
|---|---|---|---|
| CN | 104066401 | A | 9/2014 |
| CN | 203815663 | U | 9/2014 |
| CN | 105832447 | A | 8/2016 |
| CN | 105943213 | A | 9/2016 |
| EP | 1673040 | A1 | 6/2006 |
| EP | 1847234 | A1 | 10/2007 |
| EP | 1673038 | B1 | 4/2008 |
| EP | 2501334 | A1 | 9/2012 |
| EP | 2517672 | A1 | 10/2012 |
| EP | 2735283 | A1 | 5/2014 |
| EP | 2740440 | A2 | 6/2014 |
| EP | 2745812 | A1 | 6/2014 |
| EP | 2749250 | A1 | 7/2014 |
| EP | 2606851 | B1 | 11/2015 |
| EP | 3040054 | A1 | 7/2016 |
| EP | 3146993 | A1 | 3/2017 |
| EP | 3272319 | A1 | 1/2018 |
| FR | 2932979 | A1 | 1/2010 |
| JP | 2012/152549 | A | 8/2012 |
| JP | 5531016 | B2 | 6/2014 |
| JP | 5629871 | B2 | 11/2014 |
| WO | WO-97/25002 | A1 | 7/1997 |
| WO | WO-99/29262 | A1 | 6/1999 |
| WO | WO-99/34749 | A1 | 7/1999 |
| WO | WO-03/099108 | A2 | 12/2003 |
| WO | WO-2005/034809 | A1 | 4/2005 |
| WO | WO-2005/034810 | A1 | 4/2005 |
| WO | WO-2006/036690 | A1 | 4/2006 |
| WO | WO-2006/037086 | A1 | 4/2006 |
| WO | WO-2009/148594 | A1 | 12/2009 |
| WO | WO-2010/024849 | A1 | 3/2010 |
| WO | WO-2010/024880 | A1 | 3/2010 |
| WO | WO-2010/030370 | A1 | 3/2010 |
| WO | WO-2010/127040 | A1 | 11/2010 |
| WO | WO-2012/047308 | A1 | 4/2012 |
| WO | WO-2012/116368 | A2 | 8/2012 |
| WO | WO-2012/145823 | A1 | 11/2012 |
| WO | WO-2014/162306 | A2 | 10/2014 |
| WO | WO-2015/059019 | A1 | 4/2015 |
| WO | WO-2015/070792 | A1 | 5/2015 |
| WO | WO-2016/122862 | A1 | 8/2016 |
| WO | WO-2017/072168 | A1 | 5/2017 |
| WO | WO-2017/218474 | A1 | 12/2017 |
| WO | WO-2018/026768 | A1 | 2/2018 |
| WO | WO-2018/156848 | A1 | 8/2018 |
| WO | WO-2018/156849 | A1 | 8/2018 |
| WO | WO-2018/156850 | A1 | 8/2018 |
| WO | WO-2018/156851 | A1 | 8/2018 |
| WO | WO-2022/265985 | A1 | 12/2022 |

(56) References Cited

FOREIGN PATENT DOCUMENTS

| | | | |
|---|---|---|---|
| WO | WO-2022/265989 | A1 | 12/2022 |
| WO | WO-2022/0265989 | A8 | 12/2022 |

OTHER PUBLICATIONS

International Search Report and Written Opinion for International Application No. PCT/US22/33247 dated Sep. 13, 2022.

Luo et al, "Stent-grafts for the treatment of TIPS dysfunction: Fluency stent vs. Wallgrent stent," World J Gastroenterol, 19(30): 5000-5005 (2013).

Wang et al. "Preliminary experimental study on a novel adjustable sutureless aortic prosthesis" Chinese Journal of Experimental Surgery, 23(11): 1325-1327 w/ English Abstract (2006).

* cited by examiner

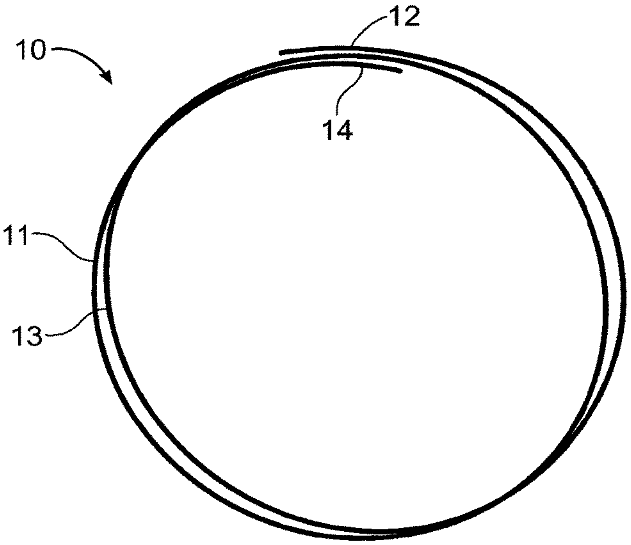
FIG. 1
FIG. 2C
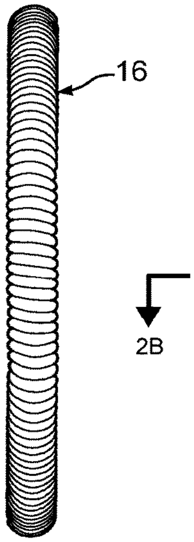
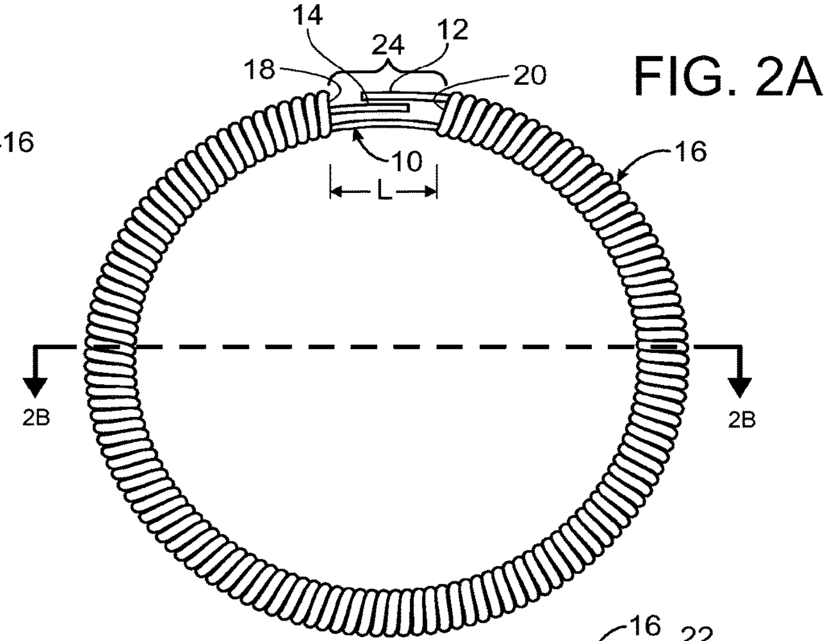
FIG. 2A
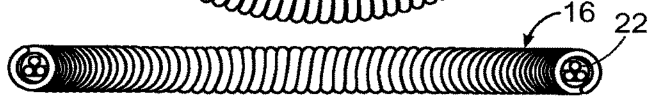
FIG. 2B
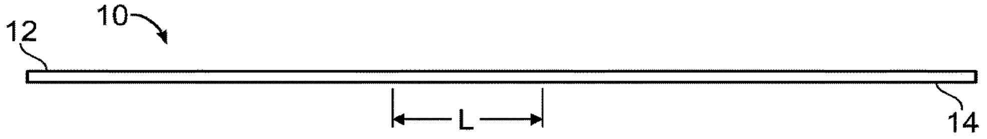
FIG. 2D

SUPPORT RING, AORTIC PROSTHESIS AND METHOD OF FORMING

CROSS-REFERENCE TO RELATED APPLICATIONS

This application is a continuation of International Application No. PCT/US2022/033239, filed on Jun. 13, 2022, which claims the benefit of U.S. Provisional Patent Application Nos. 63/210,265, filed Jun. 14, 2021 and 63/210,271, filed Jun. 14, 2021, the entire contents of which are incorporated herein by reference.

BACKGROUND

Aortic pathologies, including aortic aneurysms, are often treated by open surgical reconstruction, or alternatively, by endovascular repair, which is a minimally invasive alternative to open surgical repair. Optimizing a successful outcome of endovascular repair, however, requires assessment of the anatomy of the patient. In the case of an arterial or, more specifically, a thoracic or abdominal aortic aneurysm, an appropriate prosthesis spanning the proximal and distal end of the aneurysm ensures exclusion of the aneurysm sac by properly anchoring the prosthesis in the aorta, thereby minimizing endoleaks and movement of the prosthesis in the aorta.

In some cases, the aneurysm spans a branch blood vessel and, as a consequence, a branch prosthesis (also referred to herein a "bridging stent graft" or "bridging prosthesis") must be implanted at a fenestration in a main tubular prosthesis created for that purpose. Of particular concern in such assemblies is a need to maintain a tight seal between the fenestration of a prosthesis and a branch prosthesis extending through it to a branch blood vessel. Seepage of blood at the juncture where the branch prosthesis traverses the fenestration can have severe and even fatal consequences.

Often, however, in order to ensure a secure fit between a base of the branch prosthesis and the main tubular prosthesis at the fenestration, the branch prosthesis must extend into an interior portion defined by the main tubular prosthesis. Delivery of the branch prosthesis into an interior portion of the main tubular prosthesis, however, can damage the proximal end of the bridging stent which, in turn, can significantly interfere with the path of blood flow through the main tubular prosthesis, and passage of blood from the main tubular prosthesis into and through the branch prosthesis. Further, in some instances, the fenestration of a main tubular prosthesis is reinforced, often with a wire between the branch prosthesis and a perimeter of the fenestration. Wear between the main tubular prosthesis and the branch prosthesis, however, can be aggravated by the presence of any metal components, thereby causing a loss of integrity of fabric components of the main tubular prosthesis and the branch prosthesis that partition the metal support surrounding the fenestration and metal stents of the branch prosthesis. Such loss of integrity of fabric components can cause failure of the seal between the main tubular prosthesis and the branch prosthesis, thereby causing leakage and, ultimately, further complications, injury or death.

Therefore, a need exists for an endovascular repair devices and methods to treat aortic pathologies, such as aortic aneurysms, that overcomes or minimizes the above-mentioned problems.

SUMMARY

In one aspect, the present invention relates to a support ring for an aortic prosthesis, to an aortic prosthesis that includes a support ring, and to a method of forming a support ring for an aortic prosthesis. The present invention also relates to a graft sleeve assembly and methods of its fabrication and use. The invention is useful in treating and repairing aortic vascular damage, such as vascular damage associated with the aortic dissections and aneurysms, and damage to regions of the aorta having arterial branches that supply blood to vital organs and tissue, such as thoracic aortic aneurysms, abdominal aortic aneurysms, and thoracal abdominal aortic aneurysms and, more specifically, juxtarenal aortic aneurysms and short-neck abdominal aortic aneurysms that employ fenestrated endovascular aortic repair.

In one embodiment, a support ring for an aortic prosthesis includes a helical coil having a helical coil first end and a helical coil second end, the helical coil defining a lumen and extending in an arc, wherein the helical coil first end and the helical coil second end are in an opposing relation to each other that defines a space that is between the helical coil first end and the helical coil second end and is outside the lumen. A wire extends through the lumen and has a wire first end and a wire second end, the wire traversing the space between the helical coil first end and the helical coil second end along at least one length of the wire between the wire first end and the wire second end, and wherein the wire first end and the wire second end are secured to each other.

In another embodiment the invention is a graft sleeve assembly for an aortic prosthesis. The graft sleeve assembly includes a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, and wherein the graft sleeve proximal end defines a plane that intersects a plane defined by the graft sleeve distal end. A support ring is fixed to the graft sleeve wall that is closer to the proximal end of the graft sleeve than to the graft sleeve distal end.

In still another embodiment, the invention is an aortic prosthesis that includes a tubular graft component including a tubular graft component first end and a tubular graft component second end, and a tubular graft wall extending between the tubular graft component first end and the tubular graft component second end, the tubular graft wall defining at least one fenestration between the tubular graft component first end and the tubular graft component second end. A support ring is at the tubular wall and includes a helical coil and a wire. The helical coil has a helical coil first end and a helical coil second end, the helical coil defining a lumen and extending in an arc, wherein the helical coil first end and the helical coil second end are in an opposing relation to each other that defines a space between the helical coil first end and the helical coil second end and is outside the lumen, the helical coil being fixed to the tubular wall at the fenestration, wherein the fenestration is within the arc of the helical coil. A wire extends through the lumen and has a wire first end and a wire second end, the wire traversing the space between the wire first end and the wire second end along at least one length of the wire between the wire first end and the wire second end, and wherein the wire first end and the wire second end are secured to each other.

In yet still another embodiment the invention is an aortic prosthesis that includes a tubular graft component including a tubular graft component first end and a tubular graft component second end. A tubular graft wall extends between the tubular graft component first end and the tubular graft component second end, the tubular graft wall defining at least one fenestration between the tubular graft component first end and the tubular graft component second end. A graft sleeve having a graft sleeve proximal end, a graft sleeve distal end, and a graft sleeve wall extending between the graft sleeve proximal end and the graft sleeve distal end. The graft sleeve proximal end has a base diameter and the graft sleeve distal end has a diameter less than the base diameter, wherein the graft sleeve proximal end defines a plane that intersects a plane defined by the graft sleeve distal end, the graft sleeve wall being fixed to the tubular wall around the fenestration of the tubular graft component. A support ring is fixed to the graft sleeve wall closer to the graft sleeve proximal end than to the graft sleeve distal end. The support ring includes a helical coil having a helical coil first end and a helical coil second end, the helical coil defining a lumen and extending in an arc, wherein the helical coil first end and the helical coil second end are in an opposing relation to each other that defines a space between the helical coil first end and the helical coil second end, and is outside the lumen, the helical coil being fixed to the tubular graft wall at the fenestration, whereby the fenestration is within the arc of the helical coil. The support ring further includes a wire extending through the lumen and having a wire first end and a wire second end. The wire traverses the space between the helical coil first end and the helical coil second end along at least one length of the wire between the wire first end and the wire second end. The wire first end and the wire second end are secured to each other.

In still another embodiment, the invention is a method of forming a support ring for an aortic prosthesis. The method includes the steps of directing a wire through a lumen defined by a helical coil from a helical coil first end and through a helical coil second end that is in opposition to the helical coil first end, and across a space defined by the helical coil first end and the helical coil second end that is outside the lumen, whereby the wire traverses the space between the helical coil first end and the helical coil second end along at least one length of the wire between a wire first end and a wire second end, and securing the wire first end to the wire second end, thereby forming the support ring.

In another embodiment, the invention is a method of forming an aortic prosthesis, including the step of forming a tubular graft component having a tubular graft first end and a tubular graft second end, and a tubular graft wall extending between the tubular graft first end and the tubular graft second end, the tubular graft wall defining a fenestration. A graft sleeve is formed having a graft sleeve proximal end, a graft sleeve distal end, and a graft sleeve wall extending between the graft sleeve proximal end and the graft sleeve distal end, the graft sleeve proximal end having base diameter and the graft sleeve distal end having a diameter less than the base diameter, and wherein the graft sleeve proximal end defines a plane that intersects a plane defined by the graft sleeve distal end. The support ring is fixed to the graft sleeve wall closer to the graft sleeve proximal end than to the graft sleeve distal end, thereby forming a graft sleeve assembly of the graft sleeve and the support ring. The graft sleeve assembly is fixed to the tubular wall around the fenestration, thereby forming the aortic prosthesis.

In still another embodiment, the invention is a method of forming an aortic prosthesis. In this embodiment, the method includes forming a tubular graft having a tubular graft first end, a tubular graft second end, and a tubular wall extending between the tubular graft first end and the tubular graft second end, the tubular wall defining at least one fenestration between the tubular graft first end and the tubular graft second end. A support ring at the fenestration is formed by directing a wire through a lumen defined by a helical coil from a helical coil first end through a helical coil second end that is in opposition to the helical coil first end, and across a space defined by the helical coil first end and the helical coil second end that is outside the lumen, whereby the wire traverses the space between the helical coil first end and the helical coil second end along at least one length of the wire between a wire first end and a wire second end, and securing the wire first end into the wire second end, thereby forming the support ring. The support ring is fixed into the tubular graft at the fenestration in the tubular wall, wherein fenestration is within the arc of the helical coil, thereby forming the aortic prosthesis.

In yet another embodiment, the invention is directed to a method for implanting a branched aortic prosthesis, including the step of directing an aortic prosthesis to an aortic surgical site, the aortic prosthesis including a tubular graft component, a tubular graft first end, a tubular graft second end, and a tubular graft wall extending between the tubular graft first end and the tubular graft second end, the tubular graft wall defining at least one fenestration between the tubular graft first end and the tubular graft second end. A graft sleeve of the aortic prosthesis has a graft sleeve proximal end, a graft sleeve distal end, and a graft sleeve wall extending between the graft sleeve proximal end and the graft sleeve distal end. The graft sleeve proximal end has a base diameter and the graft sleeve distal end has a diameter less than the base diameter, wherein the graft sleeve proximal end defines a plane that intersects a plane defined by the graft sleeve distal end. The graft sleeve wall is fixed to the tubular wall around the fenestration. A support ring is fixed to the graft sleeve wall, wherein the support ring is fixed to the graft sleeve wall closer to the graft sleeve proximal end than to the graft sleeve distal end. A branch stent graft is directed distally through the graft sleeve until a branch stent graft proximal end is distal to the support ring, whereby the branched stent graft is secured by an interference fit between the branch stent graft either or both of the proximal end and the distal end, and the graft sleeve, thereby implanting the branched stent graft at the surgical site.

This invention has many advantages. For example, the support ring can be fabricated by directing a wire through a lumen of a helical coil, where the wire forms at least one complete loop that traverses a space between opposing ends of the helical coil along a length of the wire distinct from a first wire end and a second wire end that are secured to each other. By traversing the space between the helical coil first end and the helical coil second end along at least one length between the wire first end and the wire second end where they are secured to each other, the wire, in combination with the helical coil, effectively form a pulley system that diminishes the strength necessary to secure the wire first end to the second wire end against outward radial force applied to the support ring. By diminishing the force required to secure the wire first end to the wire second end, the wire first end and the wire second end can be secured to each other by a mechanism that is more easily and readily practiced, such as by crimping of relatively soft metal about the wire first end and the wire second end, than would otherwise be required in the absence of wrapping the wire in at least one additional loop beyond overlap of the first wire end and second wire end at a point where they are attached. Lack of adequate securing of the support ring against radial expansion, can cause seepage at the fenestration between the fenestration and the branch prosthesis, potentially causing failure of prosthesis assembly and consequent severe injury or death. Also, bundling wire within a helical coil avoids having to temporarily bundling wire during assembly of an aortic prosthesis, such as by tying bundled wire at several points about its periphery, thereby further simplifying manufacture and improving quality control during assembly of the aortic prosthesis prior to implantation.

In addition, the graft sleeve assembly of the invention includes a support ring fixed to a graft sleeve component at a graft sleeve wall of the graft sleeve component closer to a proximal end of the graft sleeve than to a graft sleeve distal end, thereby enabling placement of a branch stent graft, for example, within the graft sleeve distal to the support ring, or substantially distal to the support ring. Placement of a branch stent graft within the graft sleeve and securing the branch stent graft distal to the support ring, such as would occur by self-expansion or balloon expansion of stents supporting the branch stent graft in opposition to the graft sleeve wall substantially or completely avoids wear of fabric that would otherwise occur by securing the branch stent graft within a support ring fixed at a fenestration defined by a tubular graft component. Further, the support ring need not be fixed to the fenestration of the tubular graft component at all, but can be fixed to the graft sleeve wall, either in combination with being secured to the fenestration of the tubular graft component, or in the absence of being fixed to the fenestration of the tubular graft component.

Because the support ring is fixed to the graft sleeve, the support ring in the graft sleeve can be fabricated separately, as an assembly, apart from fabrication of the tubular graft component to which it is ultimately fixed. Further, the graft sleeve, having a base that defines a plane that intersects a plane defined by the graft sleeve distal end will, upon being fixed to a tubular graft component, cause the graft sleeve to have a longitudinal axis that is at an acute angle to a longitudinal axis of the tubular graft component to which it is fixed, thereby facilitating cannulation of the graft sleeve by a branch stent graft (also referred to as a “bridging stent graft”) during implementation.

Also, the support ring need not lie in a plane that is parallel to the plane defined by the graft sleeve proximal end and, therefore, can be, for example, in a plane that is orthogonal to a longitudinal axis of the graft sleeve, thereby enabling fabrication of a branch sleeve assembly, wherein the support ring is optimally placed relative to the graft sleeve proximal end, the tubular graft component, and the branch stent graft to be implanted within the graft sleeve component of the branch sleeve assembly. Further, by enabling implantation of a branch stent graft within a branch sleeve assembly of the invention, wherein a proximal end of the branch stent graft is distal to the support ring, the presence of the proximal end of the branch stent graft within the tubular graft component is avoided, thereby avoiding damage to the proximal end of the bridging stent and obstruction of blood flow from the tubular graft component into the branch stent graft.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1 is a side view of one embodiment of a wire component of a support ring of the invention, showing a wire first end and a wire second end that overlap with each other and a length of the wire between the wire first end and the wire second end that overlaps the overlapping wire first end and the wire second end.

FIG. 2A is a side view of one embodiment of a helical coil component and a wire component of a support ring of the invention for an aortic prosthesis, wherein the wire is threaded through a lumen defined by the helical coil, the helical coil having a helical coil first end and a helical coil second end, the helical coil defining a lumen and extending in an arc, wherein the wire component spans a distance between the helical coil first end and the helical coil second end along a length of the wire between the wire first end and the wire second end.

FIG. 2B is a cross-section of the support ring of FIG. 2A taken along line 2B-2B.

FIG. 2C is an end view of the support ring shown in FIG. 2A.

FIG. 2D is a side view of the wire of FIG. 1 showing the length L of the wire between a first end of the wire and the second end of the wire that extends between a first end of the helical coil and an opposing second end of the helical coil.

DETAILED DESCRIPTION

Figure 3:
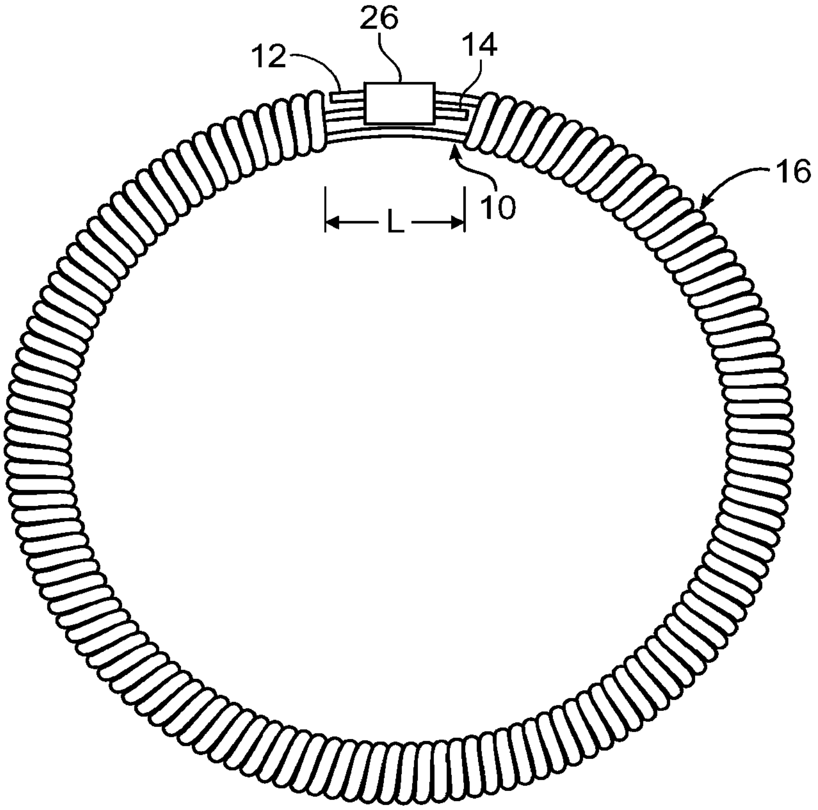
FIG. 3 is a side view of an embodiment of the support ring of the invention, wherein a connector is located at the wire first end and the wire second end.

The features and other details of the invention, either as steps of the invention or as combinations of parts of an invention, will now be more particularly described and pointed out in the claims. It will be understood that the particular embodiments of the invention are shown by way of illustration and not as to limitations of the invention. The principal features of this invention can be employed in various embodiments without departing from the scope of the invention. It will also be understood that the same number appearing in different drawings represents the same item.

The invention generally is directed to a support ring and an aortic prosthesis that includes the support ring, and a method of fabricating both the aortic prosthesis and the support ring. The aortic prosthesis is useful in treating and repairing vascular damage, such as vascular damage associated with an aortic aneurysm, including regions of the aorta having arterial branches that supply blood to vital organs and tissues, including perivisceral aortic aneurysms, such as juxtarenal aortic aneurysms and short-neck abdominal aortic aneurysms.

A description of example embodiments follows.

When reference is made to a stent graft, also referred to herein as a "prosthesis," "stent graft prosthesis," or "vascular prosthesis" to be delivered or implanted in a patient, the word "proximal" means that portion of the prosthesis or component of the prosthesis that is relatively close to the source of blood from the heart of the patient. "Distal" means that portion of the prosthesis or component of the prosthesis that is relatively far from the source of blood flow from the heart of the patient. "Cranial," as defined herein, means closer, as an absolute measure, to the heart of the patient, while "caudal," as defined herein, means farther, as an absolute measure, from the heart of the patient.

When, however, reference is made to a delivery system or component of a delivery system employed to deliver, or implant, a prosthesis, the word "proximal," as employed herein, means closer to the clinician using the delivery system. When reference is made to a delivery system or component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or delivery system.

One embodiment of a wire of a support ring of the invention is shown in FIG. 1. As shown therein, wire 10 includes wire first end 12 and second end 14. Wire 10 is coiled, thereby causing wire first end 12 to overlap wire second end 14, and also includes a length L between wire first end 12 and wire second end 14 that overlaps overlapping wire first end 12 and wire second end 14. In alternative embodiments, wire 10 can include a plurality of lengths between wire first end 12 and wire second end 14. In various embodiments, wire 10 can include 2, 3, 4, 5, 6, 7, 8, 9, or 10 lengths L between overlapping wire first end 12 and wire second end 14, as shown in FIG. 2C.

Wire 10 is formed of a suitable material, such as, for example, a shape-memory alloy or stainless steel. In one particular embodiment, wire 10 includes a shape-memory alloy. Examples of suitable shape-memory alloys include at least one of a nickel-titanium alloy, an iron-based alloy, a copper-based alloy, a zinc-based alloy, a gold-based alloy, and a high-temperature shape-memory alloy. In one particular embodiment, the shape-memory alloy is nitinol. Wire 10 can be radiopaque. Further, wire 10 has a suitable gauge, such as a thickness between about 0.004 inches and about 0.006 inches. The typical thickness is 0.004 inches, 0.005 inches, and 0.006 inches and thicknesses in between.

FIGS. 2A-D show one embodiment of a support ring of the invention prior to securing wire first end 12 to wire second end 14. As can be seen in FIG. 2A, helical coil 16 includes helical coil first end 18 and helical coil second end 20. Helical coil 16 defines lumen 22 shown in FIG. 2B, which is a cross-section of FIG. 2A taken a long line 2B-2B. FIG. 2C is an end view of wire 10 and helical coil 16 shown in FIG. 2A. Helical coil 16 is fabricated of a suitable material, such as tantalum, gold, platinum, iridium, nitinol, tungsten, and stainless steel. In one embodiment, helical coil 16 is radiopaque. In another embodiment, helical coil 16 is fabricated of a shape-memory alloy, such as nitinol.

As can be seen in FIG. 2A, helical coil first end 18 and helical coil second end 20 are in an opposing relation to each other that defines open space 24 that is between helical coil first end 18 and helical coil second end 20, and is outside of lumen 22. As can also be seen in FIG. 2A, length L of wire 10 traverses, or spans, open space 24 between helical coil first end 18 and helical coil second end 20 along at least one length L of wire 10 between wire first end 12 and wire second end 14, as seen most clearly in FIG. 2D. It should be understood that, while FIG. 2A, as shown, appears to indicate that the termini of wire at wire first end 12 and wire second end 14 within open space 24 between helical coil first end 18 and helical coil second end 20, the termini of wire 10 can, instead, be inside of lumen 22, between helical coil first end 18 and helical coil second end 20, or can extend beyond open space 24 defined by helical coil first end 18 and helical coil second end 20. In any case, length L of wire 10 between wire first end 12 and wire second end 14 completely traverses, or spans, open space 24 between helical coil first end 18 and helical coil second end 20. As stated above, FIG. 2D shows wire 10 when straightened out to illustrate the length L between wire first end 12 and wire second end 14. As can be seen in FIGS. 1 and 2A, wire 10 completes two complete loops, 11 and 13, as can be seen in FIG. 1, wherein first end 12 and second end 14 overlap. When the two loops 11, 13 of wire 10 extend through lumen 22 defined by helical coil 16, a portion of wire 10 between first end 12 and second end 14 traverses a distance 24 between first end 18 and second end 20 of helical coil 16. The portion of wire 10 between first end 12 and second end 14 that traverses distance 24 between first end 18 and second end 20 of helical coil 16 is length L. Wire 10 can have more than two loops. For example, wire 10 can have 3, 4, 5, 6, or more loops. The number of lengths L between first end 12 and second end 14 depends on the number of loops of wire 10 that extend within lumen 22 of helical coil 16. If, for example, wire 10 includes three loops, then two lengths L of wire would traverse the distance 24 between first end 18 and second end 20 of helical coil 16. The two lengths L of wire 10 would be equally spaced between first end 12 and second end 14 of wire 10. If there were four loops of wire 10, there would be three lengths L of wire 10 between first end 12 and second end 14, and so on.

Wire 10 is combined with helical coil 16 by directing either of wire first end 12 or wire second end 14 through either of helical coil first end 18 or helical coil second end 20 to emerge from the other of helical coil first end 18 or helical coil second end 20 and continue until that end is redirected through the opposing end of helical coil 16 it was first directed through, and then directed through lumen 22 defined by helical coil 16 until it emerges from the other end helical coil 16, thereby causing wire 10 to have a length L between wire first end 12 and wire second end 14 that traverses, or spans, the open space 24 between helical coil first end 18 and helical coil second end 20. In various embodiments, wire 10 can continue to be directed through lumen 22 of helical coil 16 in the same manner until a plurality of lengths L between wire first end 12 and wire second end 14 span open space 24 between helical coil first end 18 and helical coil second end 20. The number of loops, or turns of wire 10 determine the load on connector 26, discussed below, and enables the employment of a very small, thin-wall crimp made of radiopaque material, such as tantalum, which can be tacked in line with the thickness of a radiopaque marker coil. Connector 26 works in combination with the thickness of the support ring, wire 10, which typically is formed of NiTi, so it fits in helical coil 16, and yet is still able to reopen the assembly when deployed.

Figure 4:
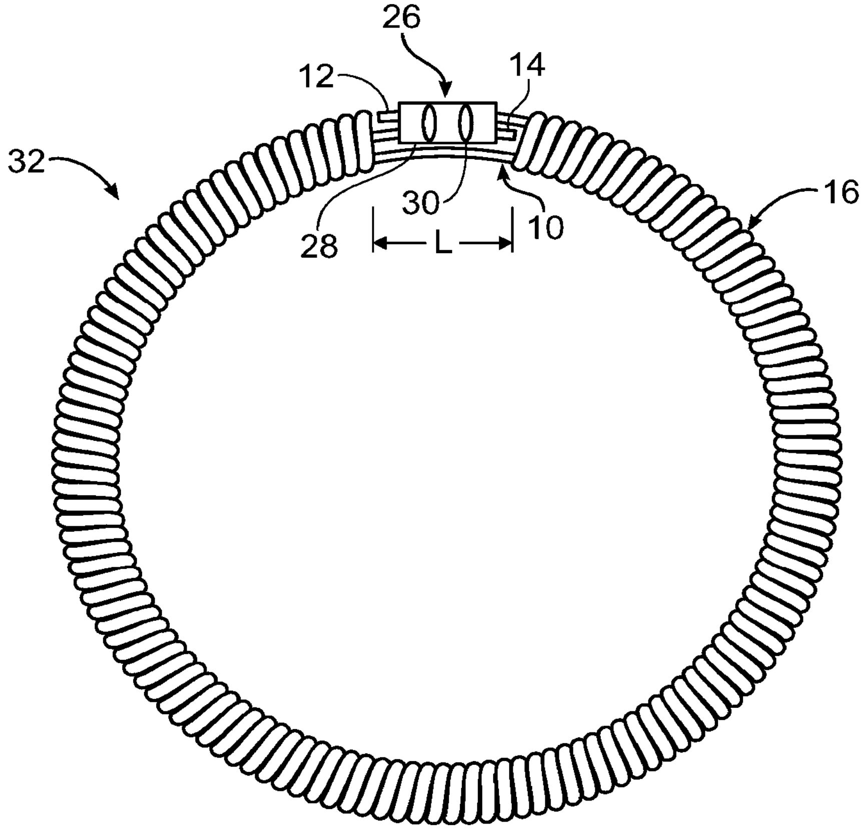
FIG. 4 is a side view of the support ring of FIG. 3 following crimping of the connector to thereby secure the wire first end and the wire second end to each other, thereby forming the support ring of the invention.

FIG. 3 is the embodiment of wire 10 and helical coil 16 shown in FIG. 2A, following the application of connector 26 over first wire end 12 and second wire end 14 before securing wire first end 12 to wire second end 14. FIG. 4 is the embodiment shown in FIG. 3 following crimping of connector 26 in two places 28, 30, thereby securing wire first end 12 to wire second end 14 and thereby forming support ring 32.

Figure 5:
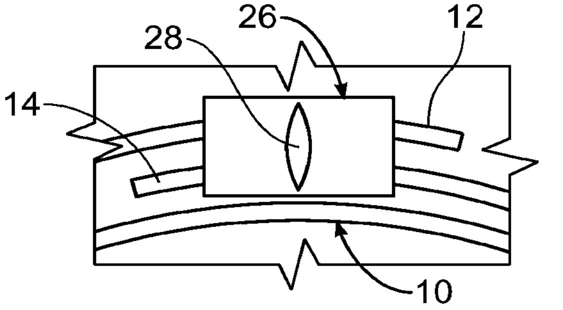
FIG. 5 is a detail of the support ring of FIG. 4, wherein connector has been crimped at one point to secure wire first end and wire second end together.

FIG. 5 is a detail of one embodiment of crimping of connector 26 to thereby secure wire first end 12 to wire second end 14. In the embodiment, shown in FIG. 5, connector 26 is crimped in only one place 28. As can be seen in FIG. 5, length L of wire 10 between wire first end 12 and wire second end 14 does not pass through connector 26.

Figure 6:
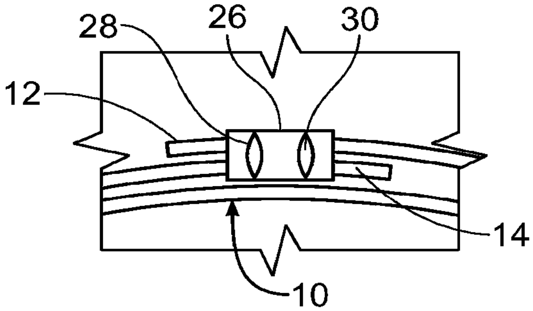
FIG. 6 is a detail of the support ring of FIG. 4, wherein the connector has been crimped at two points to thereby secure the wire first end and the wire second end together.

FIG. 6 is a detail of FIG. 4, wherein connector 26 is crimped at two places 28, 30 along its length to thereby secure wire first end 12 to wire second end 14. As in FIG. 5, length L of wire 10 between wire first end 12 and wire second end 14 is not passed through connector 26. In either case, and regardless of how wire first end 12 and wire second end 14 are fixed to each other, the combination of wire 10, helical coil 16, and connector 16 constitute embodiments of support ring 32 of the invention shown, for example, in FIG. 7A. Connector 26 is fabricated of a suitable material, such as tantalum, gold, platinum, iridium, nitinol, and stainless steel. In one embodiment, connector 26 is radiopaque.

Figure 7:
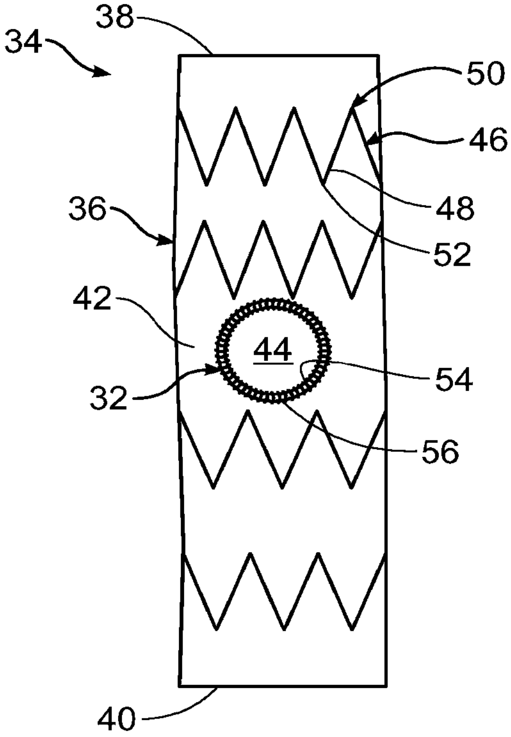
FIG. 7 is a side view of one embodiment of an aortic prosthesis of the invention, having a support ring of the invention secured to the periphery of a fenestration defined by a tubular graft wall of a tubular graft component of the aortic prosthesis.

FIG. 7 is one embodiment of an aortic prosthesis 34 of the invention, including tubular graft component 36 and support ring 32 of the invention. As shown in FIG. 7, tubular graft component 36 includes tubular graft component first end 38 and tubular graft component second end 40, and tubular graft wall 42 extending between tubular graft component first end 38 and tubular graft component second end 40. Tubular graft wall 42 defines fenestration 44 between tubular graft component first end 38 and tubular graft component second end 40. It is to be understood, however, that tubular graft wall 42 can define, in other embodiments, a plurality of fenestrations, such as at least one of 2, 3, 4 or 5 fenestrations. As shown in FIG. 7, tubular graft component 36 also includes stents 46 between tubular graft component first end 38 and tubular graft component second end 40. As shown in FIG. 7, each stent 46 includes struts 48 that are joined at opposite ends to define proximal apices 50 and distal apices 52.

Figure 7A:
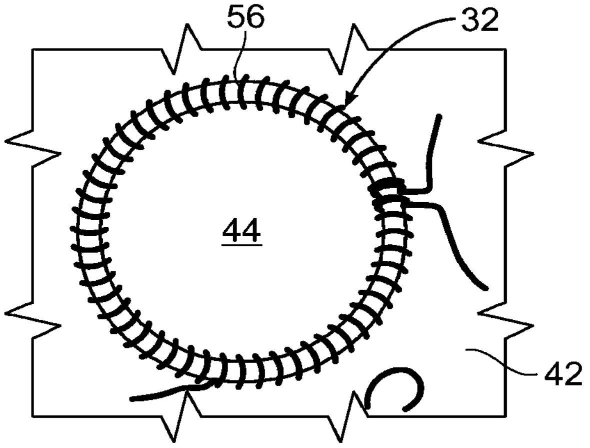
FIG. 7A is a detail of the fenestration and support ring of the prosthesis of the invention shown in FIG. 7, showing stitching of the support ring to the perimeter of the fenestration defined by the tubular graft wall of the aortic prosthesis of FIG. 7.

Support ring 32, such as that shown in FIG. 4, and described supra, is sewn to tubular graft wall 42 at perimeter 54 of fenestration 44. FIG. 7A is a detail of support ring 32 at fenestration 44 of tubular graft wall 42 shown in FIG. 7. As can be seen in FIG. 7A, in this embodiment, sutures 56 surround helical coil 16 and secure support ring 32 to tubular graft wall 42 of tubular graft component 36. Support ring 32 can be secured, such as by sewing, to an inside surface or an outside surface of tubular graft wall 42.

Figure 8:
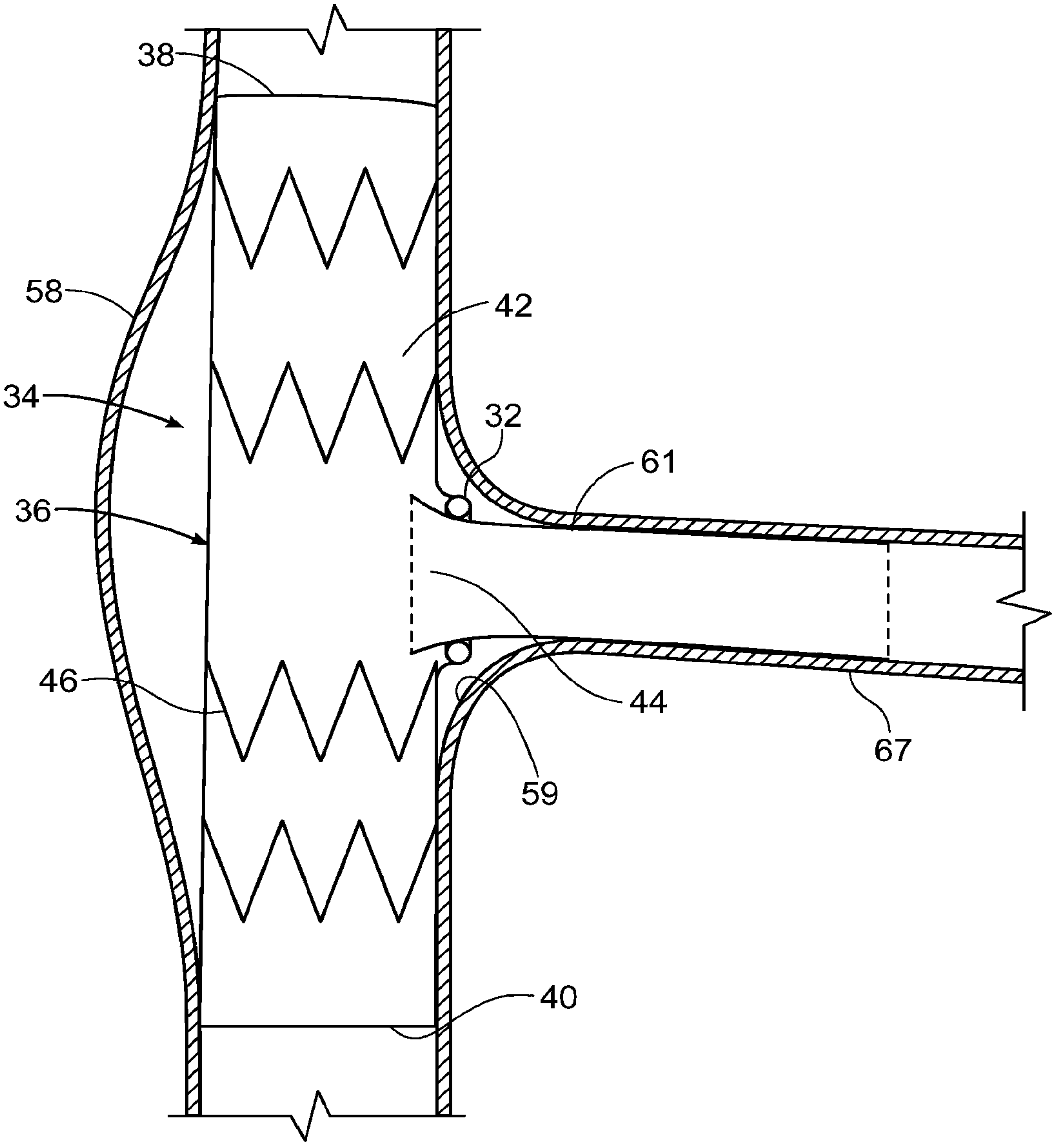
FIG. 8 is a schematic representation of one embodiment of an aortic prosthesis of the invention following implantation at an aneurysm site and following insertion of a branch prosthesis through a fenestration defined by a tubular graft wall of the aortic prosthesis, wherein a support ring of the invention seals a juncture between the branch prosthesis and the tubular graft wall of the aortic prosthesis at the fenestration defined by the tubular graft wall.

FIG. 8 is a schematic representation of one embodiment of aortic prosthesis 34 of the invention following implantation at aneurysm site 58. Branch graft 61 extends through fenestration 44 and is radially constricted by support ring 32 at tubular graft wall 42. Branch graft 61 extends from within tubular graft component 36 and distally from tubular graft component 36 through ostium 59 to arterial branch site 67 at a point distal to aneurysm site 58. It is to be understood that ostium 59 need not be part of aneurysm site 58. An advantage of the invention is that the support ring of the invention can be employed at aneurysm sites along a path of blood flow that includes at least one branch blood vessel that is not a part of the aneurysm.

Figure 9:
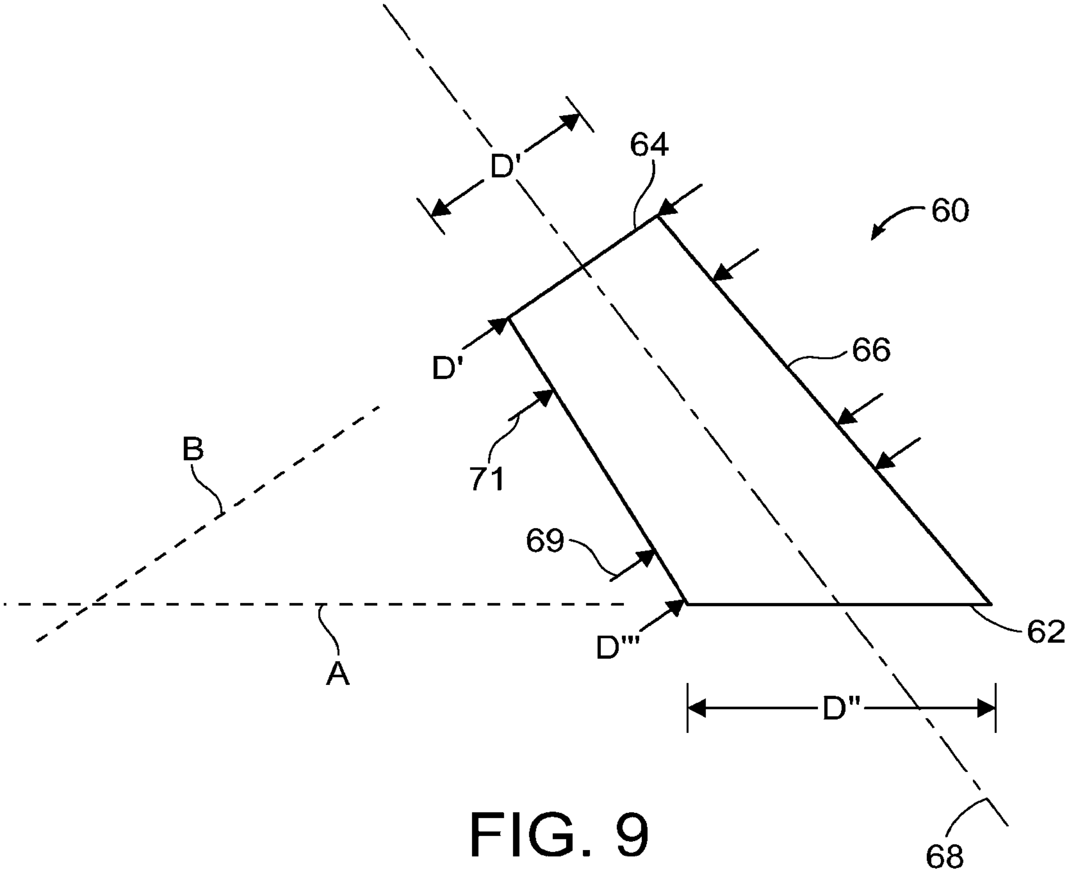
FIG. 9 is a side view of a graft sleeve of one embodiment of a branch sleeve assembly of the invention.

One embodiment of a graft sleeve of a branch sleeve assembly of the invention is shown in FIG. 9. As shown therein, graft sleeve 60 includes graft sleeve proximal end 62, graft sleeve distal end 64, and graft sleeve wall 66 extending between graft sleeve proximal end 62 and graft sleeve distal end 64. Graft sleeve distal end 64 has a diameter D' and graft sleeve proximal end 62 has a base diameter D". Graft sleeve proximal end 62 base diameter D" is greater than D' of graft sleeve distal end 64. Graft sleeve proximal end 62 defines plane A that intersects plane B defined by graft sleeve distal end 64. Although not necessary, graft sleeve wall 66 is tapered, wherein diameter D''' of graft sleeve 60 at a point proximal to graft sleeve distal end 64 is in a plane orthogonal to longitudinal axis 68 of graft sleeve 60 and is greater than diameter D' of graft sleeve distal end 64. In one embodiment, graft sleeve 60 is conical, or tapered. In one specific embodiment of a conical shape of graft sleeve 60, an orthogonal first cross-section 69 of graft sleeve 60 has a wider diameter than an orthogonal second cross-section 71 of graft sleeve 60 at a point along longitudinal axis 68 that is distal to the orthogonal first cross-section 69 of graft sleeve 60.

Figure 10:
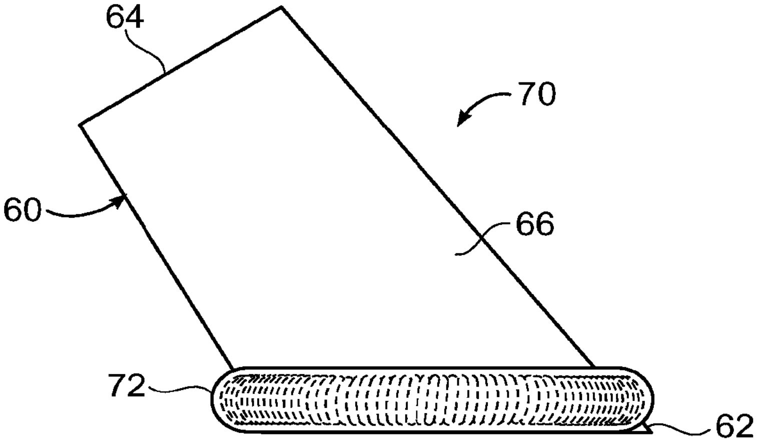
FIG. 10 is a side view of a branch sleeve assembly of the invention, wherein a support ring has been fixed to the graft sleeve wall of a graft sleeve represented in FIG. 9.

FIG. 10 is a side view of one embodiment of branch sleeve assembly 70 of the invention, including graft sleeve 60 of FIG. 9 and support ring 72 fixed to graft sleeve wall 66 closer to graft sleeve proximal end 62 than to graft sleeve distal end 64. Support ring 72 can be either on an outside surface of graft sleeve 60, or within a lumen defined by graft sleeve 60, as shown in FIG. 10. Support ring 72 is of a suitable construction, such as is known in the art of rings that are fixed to fenestrations defined by tubular grafts employed in aortic aneurysm repair. In one embodiment, support ring 72 is an assembly that includes a radiopaque component. Examples of suitable materials of radiopaque component of support ring 72 include, for example, at least one of gold, platinum, iridium, and tantalum.

Figure 11:
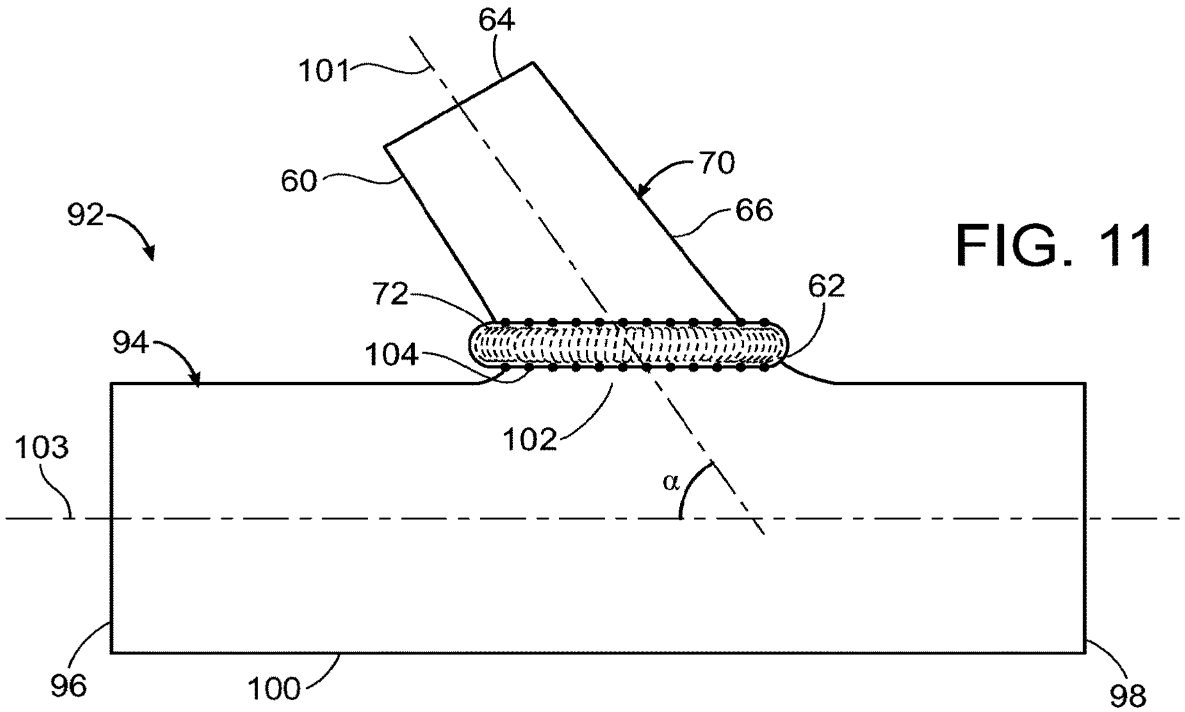
FIG. 11 is a side view of the branch sleeve assembly of FIG. 10 after being secured to the perimeter of a fenestration of a tubular graft component.

In another embodiment, shown in FIG. 11, the invention is aortic prosthesis 92 that includes tubular graft component 94 having tubular graft component first end 96, tubular graft component second end 98, and tubular graft wall 100 extending between the tubular graft component first end 96 and the tubular graft component second end 98. Tubular graft wall 100 defines at least one fenestration 102 between tubular graft component first end 96 and tubular graft component second end 98, wherein graft sleeve wall 66 of branch sleeve assembly 70 is fixed to tubular graft wall 100 around fenestration 102.

As shown in FIG. 11, branch sleeve assembly 70 is fixed to tubular graft wall 100 around fenestration 102 by sutures 104 extending about fenestration 102 and graft sleeve proximal end 62. In another embodiment, not shown, support ring 72 is fixed to tubular graft wall 100 at fenestration 102, wherein fenestration 102 is within the arc of support ring 72, in addition to support ring 72 also being fixed to graft sleeve proximal end 62. In another embodiment, also not shown, tubular graft component 64 is a stent graft. In one embodiment, longitudinal axis 101 of branch sleeve assembly 70 intersects longitudinal axis 103 of tubular graft wall 100 at an angle α. The range of angle α can be, for example, in a range of 0° and 180°, such as an angle of 30°, 60°, 90°, 120°, or 150°.

Figure 12:
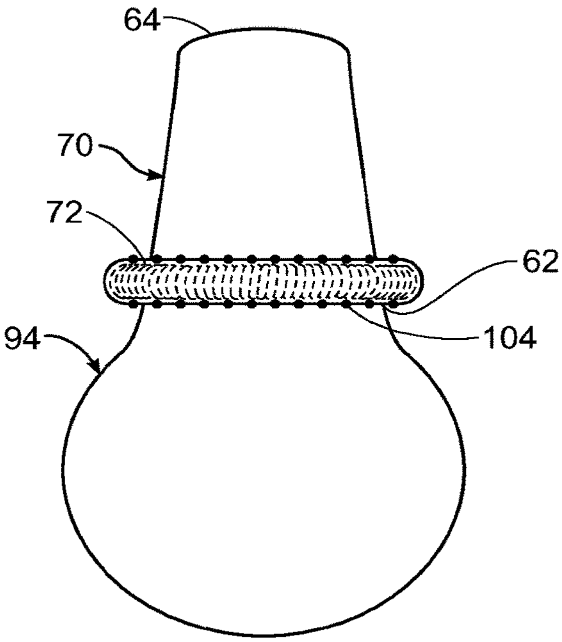
FIG. 12 is a view of the branch sleeve assembly secured to a tubular graft component, as shown FIG. 11, but viewed along a line of sight parallel to a longitudinal axis of the tubular graft component.

The embodiment of the invention shown in FIGS. 11 and 12 includes aortic prosthesis 92 having; as component parts, tubular graft component 94, graft sleeve 60 and support ring 72. In one specific embodiment, support ring 72 is fixed to graft sleeve wall 66, and includes helical coil 16 defining lumen 22, shown in FIG. 2A, and wire 10, shown in FIGS. 1-6 extending through lumen 22, and includes a length L of wire 10 traversing space (not shown) between helical coil first end 18 and helical coil second end 20, and wherein wire first end 12 and wire second end 14 are secured to each other, as shown in FIGS. 4-6, and discussed in detail above.

In another embodiment, the invention is a method of forming aortic prosthesis 92, such as is shown in FIG. 11, that includes the step of forming tubular graft component 94 having tubular graft component first end 96 and tubular graft component second end 98. Tubular wall 100 extends between the tubular graft component first end 96 and the tubular graft component second end 98, wherein the tubular graft wall 100 defines fenestration 102, such as is shown in FIG. 11. Graft sleeve 60 is formed having a graft sleeve proximal end 62, graft sleeve distal end 64, and graft sleeve wall 66 extending between the graft sleeve proximal end 62 and graft sleeve distal end 64, as shown in FIGS. 9 and 10. Graft sleeve proximal end 62 has a base diameter and graft sleeve distal end 64 has a diameter less than that of the base diameter of graft sleeve proximal end 62, as described above with respect to FIG. 9, such as at an acute angle, wherein the graft sleeve proximal end 62 defines plane A that intersects plane B defined by graft sleeve distal end 64, as also described above with respect to FIG. 9. Support ring 72 is fixed to the graft sleeve wall 66 closer to graft sleeve proximal end 62 than to the graft sleeve distal end 64, thereby forming graft sleeve assembly 70, as described above with reference to FIG. 10. Resulting graft sleeve assembly 70 is fixed to tubular graft wall 100 around fenestration 102, thereby forming aortic prosthesis 92, as represented above in FIGS. 11 and 12.

In an alternative embodiment, graft sleeve 60 is fixed to tubular graft component 100 and around fenestration 102 by a suitable means, such as by stitching or by use of an adhesive, and then support ring 72 is fixed to an outside surface of graft sleeve 60 where graft sleeve 60 is fixed to tubular graft component 100, or distal to where graft sleeve 60 is fixed to tubular graft component 94, by suitable means, such as by stitching. Distal end 64 of graft sleeve 60 can be either cranial or caudal to proximal end 62 of graft sleeve 60.

Stent grafts can be implanted at a surgical site that spans an aneurysm, in particular in the perivisceral segment of the aorta, by suitable methods, such as is known in the art. Following implantation, bridging stents can be delivered through the fenestration, fenestration ring and into a branch of the aorta, such a renal, superior mesenteric or celiac arteries. Suitable delivery devices for implanting stent grafts are described, for example, in U.S. Patent Application Nos: 63/111,357 and 63,153,701, and U.S. Ser. No. 210,381, the relevant teachings of all of which are hereby incorporated by reference in their entirety.

In one embodiment, support ring 72 is formed by a method including directing wire 10 through lumen 22 defined by helical coil 16, shown in FIGS. 1, and 2A-2C, extending in an arc from helical coil first end 18 through helical coil second end 20 in opposition to the helical coil first end 18, and across length L of the space defined by helical coil first end 18 and helical coil second end 20 that is outside lumen 22 defined by helical coil 16, whereby wire 10 traverses length L of the space between helical coil first end 18 and helical coil second end 20 along at least one length L of wire 10 between wire first end 12 and wire second end 14, and securing wire first end 12 to wire second end 14, thereby forming support ring 32, as represented, for example, above, and as described above, with reference to FIG. 4. In one embodiment, the method further includes the step of fixing the support ring 72, shown in FIGS. 11 and 12, to tubular graft component 94 at fenestration 102 in tubular graft wall 100 of tubular graft component 94, wherein fenestration 102 is within the arc of support ring 72, thereby forming another embodiment of aortic prosthesis 92 of the invention.

Figure 13:
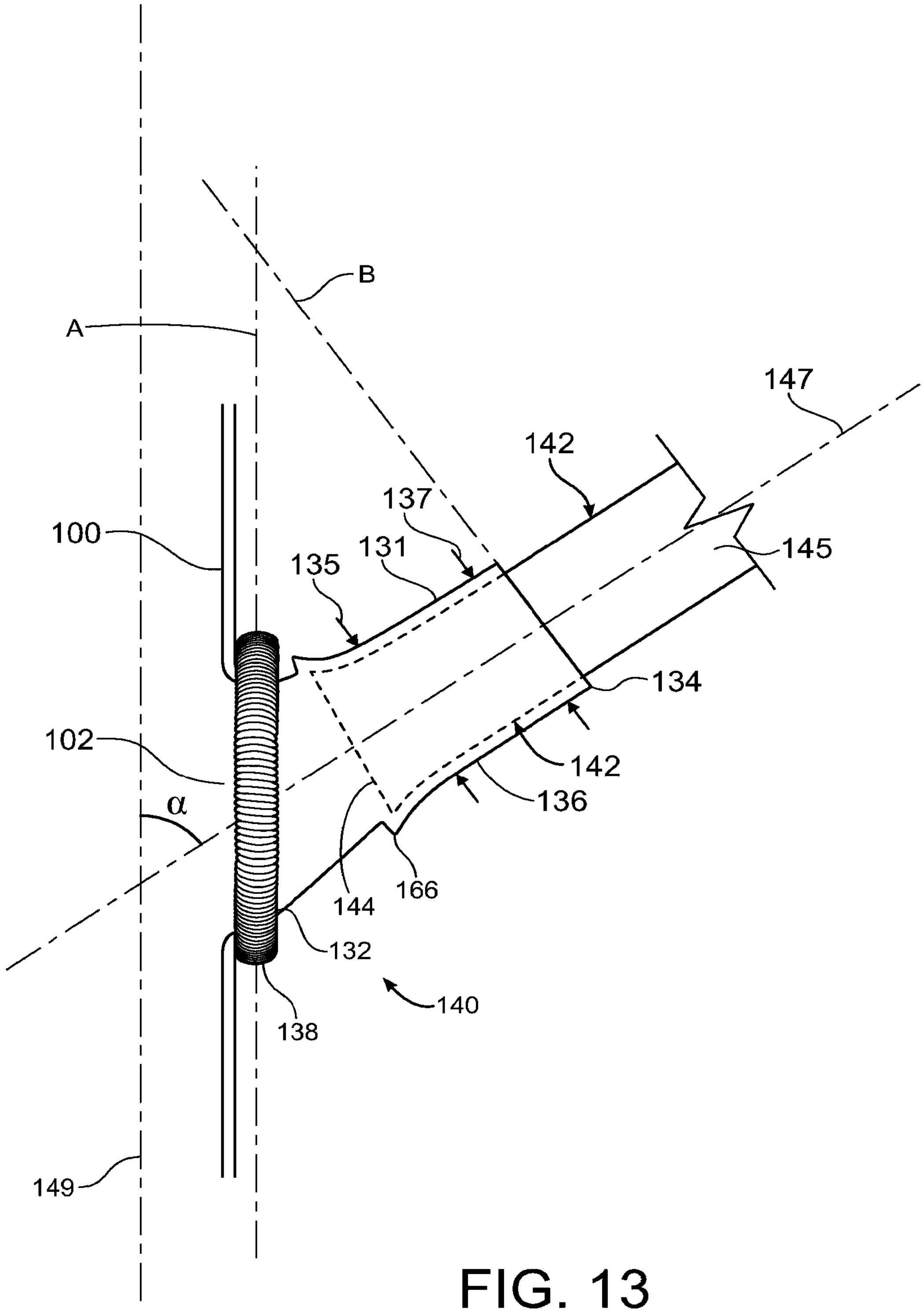
FIG. 13 is a side view of an embodiment of the invention, wherein a support ring is fixed to a graft sleeve, the proximal end of which is fixed to the perimeter of a fenestration of a tubular graft, and where a branch stent graft is fixed at the graft sleeve by an interference fit.

In another embodiment, shown in FIG. 13, the invention is graft sleeve assembly 140, having graft sleeve 131, which includes graft sleeve proximal end 132, graft sleeve distal end 134, and graft sleeve wall 136 extending between the graft sleeve proximal end 132 and graft sleeve distal end 134. Graft sleeve proximal end 132 has a base diameter and graft sleeve distal end 134 has a diameter less than that of the base diameter of graft sleeve proximal end 132. Graft sleeve proximal end 132 defines plane A that intersects plane B defined by graft sleeve distal end 134. In an embodiment, graft sleeve 131 is conical, or tapered, whereby the diameter of an orthogonal first cross-section 135 of graft sleeve 131 is wider than an orthogonal second cross-section 137 of graft sleeve 131 distal to orthogonal first cross-section 135. Support ring 138 of graft sleeve assembly 140 is fixed to the graft sleeve wall 136 closer to graft sleeve proximal end 132 than to the graft sleeve distal end 134, thereby forming graft sleeve assembly 140. Support ring 138 can be either on an outside surface of graft sleeve 131, as shown, or on an inside surface of graft sleeve 131. Graft sleeve 131 is fixed to tubular graft component 100 about a perimeter of fenestration 102 by suitable means, such as by stitching or by adhesive. Branch stent graft 142 is implanted by directing branch stent graft 142 through fenestration 102 and into graft sleeve 131 until distal end 145 of branch stent graft 142 extends from distal end 134 of graft sleeve 131, and proximal end 144 of branch stent graft 142 is fixed at graft sleeve 131 by an interference fit with graft sleeve 131, as indicated by ridge mark 166.

In an alternative embodiment, support ring 138 is fixed directly to tubular graft component 100 at a perimeter of fenestration 102 by suitable means, such as by stitching. Distal end 134 of graft sleeve 131 can be either cranial or caudal to proximal end 132 of graft sleeve 131. In an embodiment, branch stent graft 142 is flared at proximal end 144, as shown in FIG. 13. While proximal end 144 of branch stent graft 142 is always receiving blood that exits branch stent graft 142 through distal end 145, graft sleeve 131 and branch stent graft 142 collectively define longitudinal axis 147 that intersects with longitudinal axis 149 of tubular graft component 100 at angle α. Angle α can vary from 0° to 180°, meaning that, following implantation, distal end 145 of branch stent graft 142 can be located cranially or caudally relative to proximal end 144 of branch stent graft 142. Typical angles α between 0° and 1800 are, for example, 30°, 60°, 90°, 120°, and 150°.

In this instance, support ring 138 extends around graft sleeve 131. Branch stent graft 142 is implanted by directing branch stent graft 142 through fenestration 102 and into graft sleeve 131 until branch stent graft 142 extends from distal end 134 of graft sleeve 131, and proximal end 144 of branch stent is fixed at graft sleeve 131 by an interference fit with graft sleeve 131, as indicated by ridge mark 166.

Figure 14:
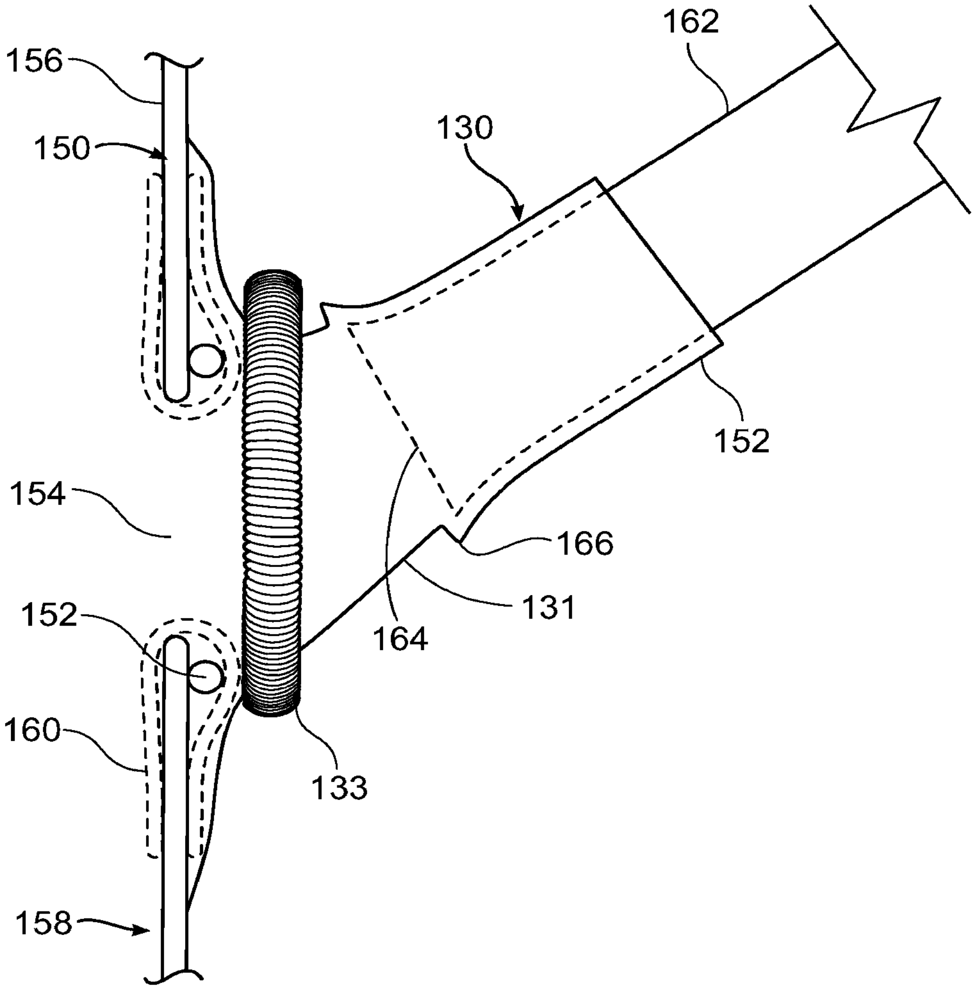
FIG. 14 is a side view of another embodiment of the invention, wherein a graft sleeve, having a support ring fixed to an outside surface of the graft sleeve, wherein the graft sleeve is fixed to a liner covering a sealing ring at a fenestration of a tubular graft, and a branch stent graft secured at the graft sleeve by an interference fit of the branch stent graft with the graft sleeve.

In still another embodiment, shown in FIG. 14, graft sleeve assembly 130 is fixed to assembly 150, such as is described in U.S. Ser. No. 63/210,258, the relevant teachings of which are incorporated herein by reference in their entirety. More specifically, ring 152 extends around fenestration 154 defined by tubular graft component 156, and wherein ring 152 is secured between one side of the tubular graft component 156 of stent graft 158 and liner 160, and wherein liner 160 extends through fenestration 154. As shown in FIG. 14, ring 152 is optional when support ring 133 is present. Typically, support ring 133 is that shown in FIG. 4 and described above. In another embodiment, ring 152 is the support ring shown in FIG. 4 and described above, and support ring 133 is not present. In still another embodiment, ring 152 has a different configuration from that of FIG. 4. For example, FIG. 4 can be a series of wind of a suitable wire, such as a nitinol wire. Alternatively, ring 152 can be a continuous or discontinuous ring of radiopaque markers. In yet another embodiment, ring 152 is a support ring, such as that described with reference to FIG. 4, and item 133 of FIG. 14 is present, but has an alternate configuration, such as a series of winds of a suitable material, such as nitinol, or a continuous or discontinuous ring of radiopaque markers.

Graft sleeve assembly 130 is fixed by suitable means, such as by stitching or use of adhesive, to a portion of liner 160 that is external to tubular graft component 156. Graft sleeve 131 of graft sleeve assembly 130 is fixed to liner 160 by suitable means, such as by stitching or by an adhesive. Support ring 133 is fixed to the proximal end of graft sleeve 131 by suitable means, such as by stitching. Alternatively, in another embodiment, not shown, graft sleeve 131 can be fixed directly to tubular graft component 156. Branch stent graft 162 is directed through fenestration 154 and into graft sleeve 131 of graft sleeve assembly 130 until proximal end 164 of branch stent graft 162 is in interfering relation with graft sleeve 131, as shown by ridge mark 166.

Examples of tubular graft components, and methods of their implantation at an aneurysm site are such as are known in the arts, such as is described in the relevant teachings of all patents, published applications, and references cited herein, all of which are incorporated by reference in their entirety. Stent grafts can be implanted at a surgical site that spans an aneurysm, in particular in the perivisceral segment of the aorta, by suitable methods, such as is known in the art. Following implantation, bridging stents can be delivered through the fenestration, fenestration ring and into a branch of the aorta, such a renal, superior mesenteric or celiac arteries. Suitable delivery devices for implanting stent grafts are described, for example, in U.S. Patent Application Nos: 63/111,357 and 63/153,701, and U.S. Ser. No. 63/210,381, the relevant teachings of all of which are hereby incorporated by reference in their entirety.

Figure 15:
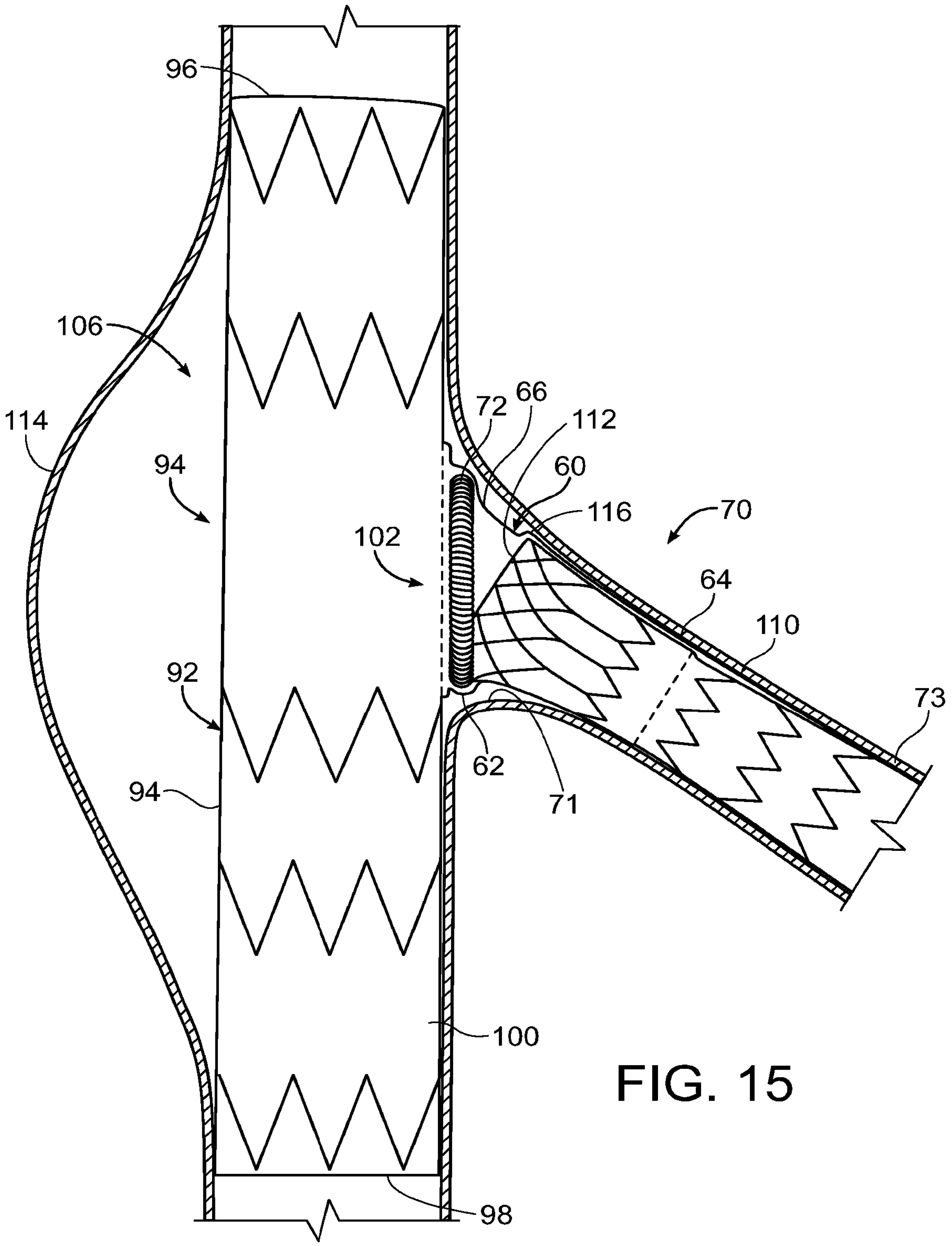
FIG. 15 is a side view of an aortic prosthesis of the invention after being implanted within an aneurysm site of a patient, and after a fenestration defined by a tubular graft component and branch sleeve assembly of the aortic prosthesis has been cannulated, and a branch stent graft has been implanted in the branch sleeve assembly, whereby the branch stent graft is secured within the branch sleeve assembly by an interference fit between the branch sleeve assembly and a proximal end of the branch stent graft, and wherein the branch sleeve projects caudally from a proximal end to a distal end of the graft sleeve.
Figure 16:
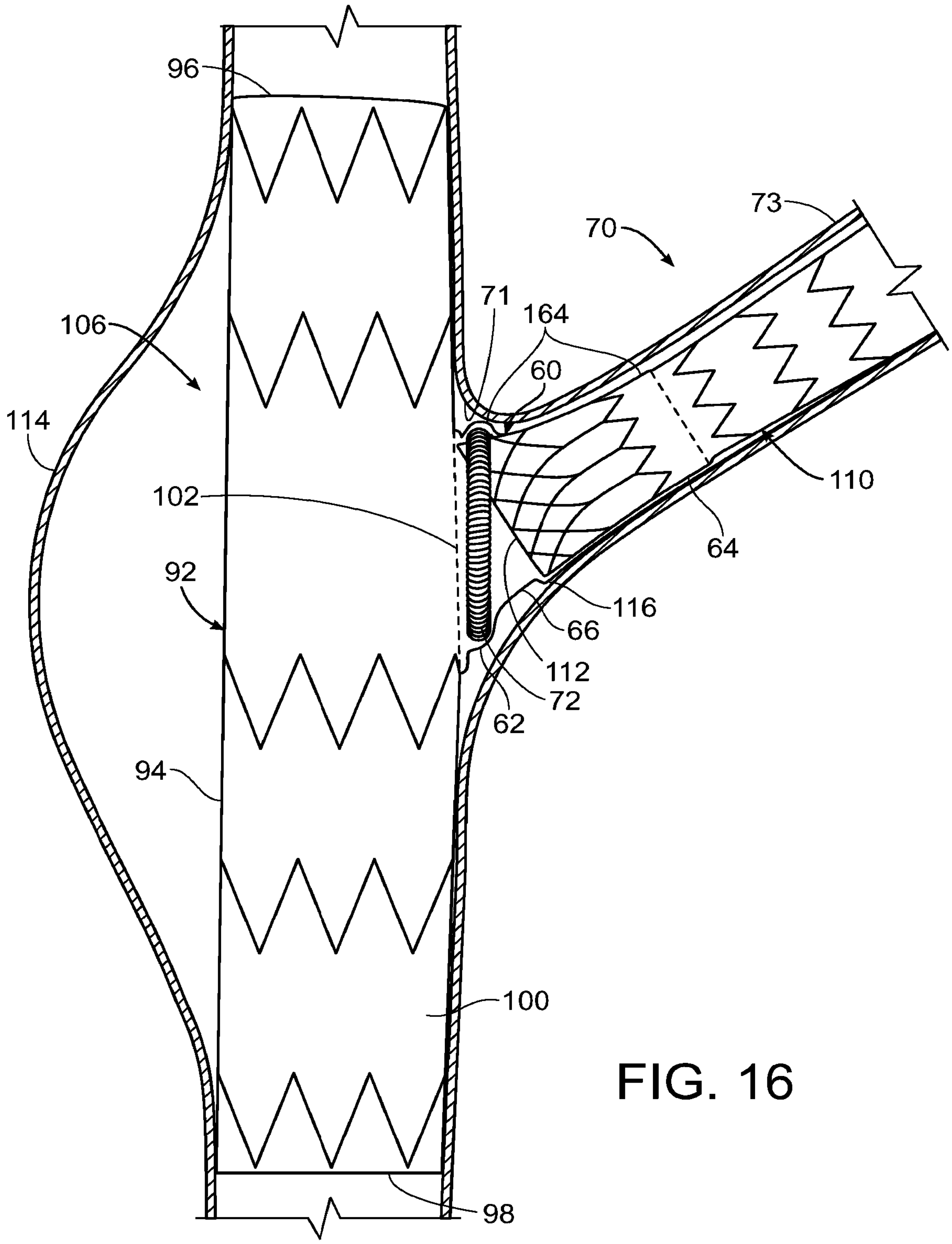
FIG. 16 is a side view of an aortic prosthesis of the invention after being implanted within an aneurysm of a patient, and after a fenestration defined by a tubular graft component and branch sleeve assembly of the aortic prosthesis has been cannulated, and a branch stent graft has been implanted in the branch sleeve assembly, whereby the branch stent graft is secured within the branch sleeve assembly by an interference fit between the branch sleeve assembly and a proximal end of the branch stent graft, and wherein the graft sleeve projects cranially from a proximal end to a distal end of the graft sleeve.

In another embodiment, the invention is a method for implanting a branched aortic prosthesis, such as branched aortic prosthesis 106, shown in FIG. 15, at aneurysm site 114, wherein branch sleeve assembly 70 includes graft sleeve 60 extending through ostium 71, which is essentially flush with tubular graft component 94, and into aortic branch 73, and is oriented caudally from graft sleeve proximal end 72 to graft sleeve distal end 64. Alternatively, as can be seen in FIG. 16, branch sleeve assembly 70 can be oriented cranially from graft sleeve proximal end 62 to graft sleeve distal end 64, wherein graft sleeve 60 extends through ostium 71, which is essentially flush with tubular graft component 94, and into aortic branch 73. In either FIG. 15 or FIG. 16, implanting branched aortic prosthesis 106 includes directing aortic prosthesis 92 to an aortic surgical site, wherein aortic prosthesis 92 includes tubular graft component 94 including tubular graft component first end 96 and a tubular graft component second end 98, wherein tubular graft component includes tubular graft wall 100 that extends between tubular graft component first end 96 and tubular graft component second end 98. Tubular graft wall

100 defines at least one fenestration 102 between the tubular graft component first end 96 and the tubular graft component second end 98.

Figure 17:
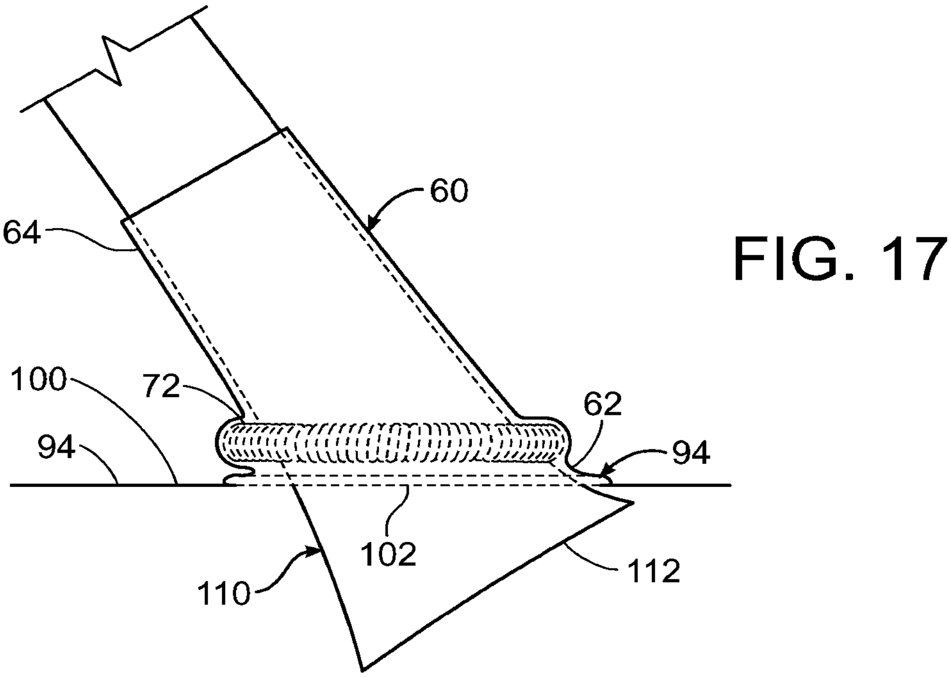
FIG. 17 is one embodiment of placement of a branch stent graft at least partially implanted within the tubular graft component and branch sleeve assembly of FIGS. 11 and 12, wherein a proximal end of the branch stent graft extends within an interior lumen defined by the tubular graft component.
Figure 18:
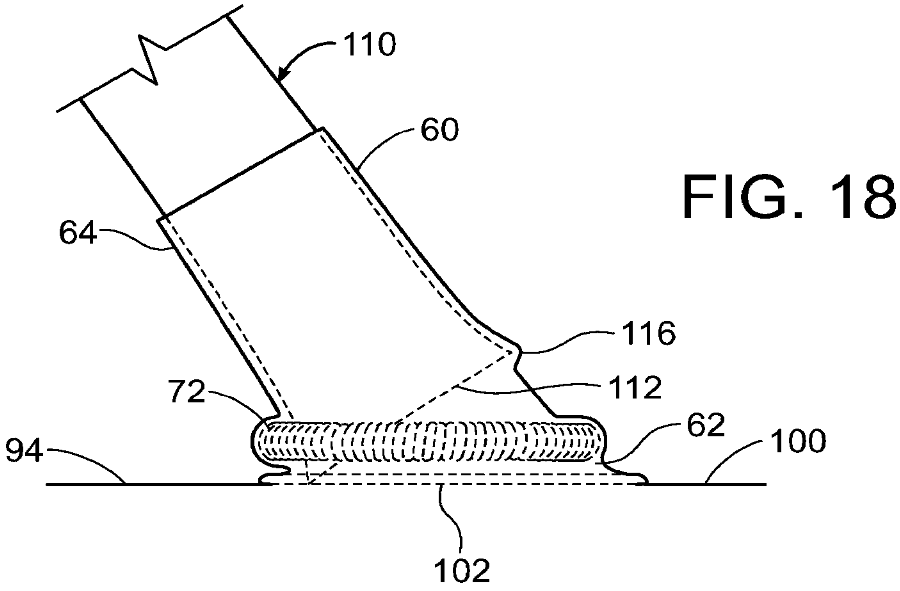
FIG. 18 is a side view of the branch stent graft of FIG. 17 after having been directed further into the branch sleeve assembly of the invention, whereby a proximal end of the branch stent graft is secured by an interference fit with the graft sleeve wall of the graft sleeve, and wherein the proximal end of the branch stent graft no longer interferes with the path of flow through the tubular graft component nor risks potential damage to the proximal end of the branch stent graft that obstructs the flow of blood from the tubular graft component into the branch stent graft implanted within the branch sleeve assembly of the invention.

As shown in the progression from FIG. 17 to FIG. 18, branch stent graft 110 is directed distally through graft sleeve proximal end 62 until at least a portion of branch stent graft proximal end 62 is distal to support ring 72, whereby branch stent graft 110 (also referred to herein a "bridging stent graft" or "bridging prosthesis") is secured by an interference fit 116 between branch stent graft proximal end 112 and graft sleeve 60, shown in FIG. 18, thereby implanting branch stent graft 110 at surgical site 114, as shown in FIGS. 15 and 16.

In one particular embodiment of the method of implanting support ring 72 of the invention includes the step of fixing support ring 72 to tubular graft wall 100 of tubular graft component 100 at fenestration 102, as shown in FIG. 11, wherein fenestration 102 is within the arc of supporting ring 72. Graft sleeve 60 can then be fixed to tubular graft component 100 at fenestration 102 over support ring 72 by a suitable means, such as stitching or by use of adhesive.

In an alternative embodiment, graft sleeve 60 is fixed to tubular graft component 100 and around fenestration 102 by a suitable means, such as by stitching or by use of an adhesive, and then support ring 72 is fixed to an outside surface of graft sleeve 60 where graft sleeve 60 is fixed to tubular graft component 100, or distal to where graft sleeve 60 is fixed to tubular graft component 94, by suitable means, such as by stitching. Distal end 64 of graft sleeve 60 can be either cranial or caudal to proximal end 62 of graft sleeve 60.

In a further embodiment, the invention is a support ring for an aortic prosthesis, comprising (a) a helical coil having a helical coil first end and a helical coil second end, the helical coil defining a lumen and extending in an arc, wherein the helical coil first end and the helical coil second end are in an opposing relation to each other that defines a space that is between the helical coil first end and the helical coil second end and is outside the lumen; and (b) a wire extending through the lumen and having a wire first end and a wire second end, the wire traversing the space between the helical coil first end and the helical coil second end along at least one length of the wire between the wire first end and the wire second end, and wherein the wire first end and the wire second end are secured to each other.

In various embodiments, the support ring further includes a crimped connector at the wire, whereby the wire first end and the wire second end of the wire are secured to each other.

In various embodiments, the crimped connector is in the space between the helical coil first end and the helical coil second end.

In various embodiments, crimped connector includes at least one of tantalum, gold, platinum, iridium, nitinol, and stainless steel.

In various embodiments, the helical coil is radiopaque.

In various embodiments, the helical coil includes at least one of tantalum, gold, platinum, iridium, nitinol, tungsten, and stainless steel.

In various embodiments, the wire includes at least one of a shape-memory alloy and stainless steel.

In various embodiments, the wire includes a shape-memory alloy.

In various embodiments, the shape-memory alloy includes at least one of a nickel-titanium alloy, an iron-based alloy, a copper-based alloy, a zinc-based alloy, a gold-based alloy, and a high-temperature shape-memory alloy.

In various embodiments, the shape-memory alloy includes nitinol.

In various embodiments, the wire traverses the space between the helical coil first end and the helical coil second end at a plurality of lengths between the wire first end and the wire second end.

In various embodiments, the wire traverses the space between the helical coil first end and the helical coil second end at two, three, four, five, six, seven, eight, nine, or ten lengths along the wire.

In various embodiments, the support ring further includes a tubular graft having a tubular graft first end, a tubular graft second end, and a tubular graft wall extending between the tubular graft first end and tubular graft second end, the tubular graft wall defining at least one fenestration between the tubular graft first end and the tubular graft second end, wherein the helical coil is fixed to the tubular graft wall at the fenestration, and wherein the fenestration is within the arc of the helical coil.

In various embodiments, the tubular graft is a stent graft.

In various embodiments, the support ring further includes a branch graft extending through the fenestration of the stent graft.

In various embodiments, the radial diameter of the branch graft at the fenestration is constrained.

In yet another embodiment, the invention is a branch sleeve assembly for an aortic prosthesis, comprising: (a) a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, and wherein the graft sleeve proximal end defines a plane that intersects a plane defined by the graft sleeve distal end; and (b) a support ring fixed to the graft sleeve wall that is closer to the proximal end of the graft sleeve than to the graft sleeve distal end.

In various embodiments, the graft sleeve is tapered, wherein a cross-sectional diameter is greater proximal to the graft sleeve distal end than at the graft sleeve distal end.

In various embodiments, the support ring is an assembly that includes a radiopaque component.

In various embodiments, the radiopaque component includes at least one of gold, platinum, iridium, and tantalum.

In various embodiments, the support ring includes: (a) a helical coil having a helical coil first end and a helical coil second end, the helical coil defining a lumen and extending in an arc, wherein the helical coil first end and the helical coil second end are in an opposing relation to each other that defines a space that is between the helical coil first end and the helical coil second end, and is outside the lumen; and (b) a wire extending through the lumen and having a wire first end and a wire second end, the wire traversing the space between the helical coil first end and the helical coil second end along at least one length of the wire between the wire first end and the wire second end, and wherein the wire first end and the wire second end are secured to each other.

In various embodiments, the helical coil is the radiopaque component.

In various embodiments, the wire traverses the space between the helical coil first end and the helical coil second end at a plurality of lengths between the wire first end and the wire second end.

In various embodiments, the wire traverses the space between the helical coil first end and the helical coil second end at two, three, four, five, six, seven, eight, nine, or ten lengths along the wire.

In various embodiments, the branch sleeve assembly further includes a tubular graft having a tubular graft first end, a tubular graft second end, and a tubular graft wall extending between the tubular graft first end and tubular graft second end, the tubular graft wall defining at least one fenestration between the tubular graft first end and the tubular graft second end, wherein the graft sleeve wall is fixed to the tubular graft wall around the fenestration.

In various embodiments, the support ring is fixed to the tubular graft wall at the fenestration, and wherein the fenestration is within the arc of the helical coil.

In various embodiments, the tubular graft is a stent graft.

In various embodiments, the branch sleeve assembly further includes a branch stent graft having a branch stent graft proximal end and a branch stent graft distal end, the branch stent graft extending distally from within the graft sleeve distal end, the branch stent graft being secured to the graft sleeve by an interference fit between the branch stent graft and the graft sleeve.

In various embodiments, the branch stent proximal end is distal to the support ring.

In an additional embodiment, the invention is an aortic prosthesis, comprising: (a) a tubular graft component including a tubular graft component first end and a tubular graft component second end, and a tubular graft wall extending between the tubular graft component first end and the tubular graft component second end, the tubular graft wall defining at least one fenestration between the tubular graft component first end and the tubular graft component second end; and (b) a support ring at the tubular wall, the support ring including (i) a helical coil having a helical coil first end and a helical coil second end, the helical coil defining a lumen and extending in an arc, wherein the helical coil first end and the helical coil second end are in an opposing relation to each other that defines a space between the helical coil first end and the helical coil second end and is outside the lumen, the helical coil being fixed to the tubular wall at the fenestration, wherein the fenestration is within the arc of the helical coil, and (ii) a wire extending through the lumen and having a wire first end and a wire second end, the wire traversing the space between the wire first end and the wire second end along at least one length of the wire between the wire first end and the wire second end, and wherein the wire first end and the wire second end are secured to each other.

In yet another embodiment, the invention is an aortic prosthesis, comprising: (a) a tubular graft component including a tubular graft component first end and a tubular graft component second end, and a tubular graft wall extending between the tubular graft component first end and the tubular graft component second end, the tubular graft wall defining at least one fenestration between the tubular graft component first end and the tubular graft component second end; (b) a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, and wherein the graft sleeve proximal end defines a plane that intersects a plane defined by the graft sleeve distal end, wherein the graft sleeve wall is fixed to the tubular wall around the fenestration; and (c) a support ring fixed to the graft sleeve wall, wherein the support ring is fixed to the graft sleeve wall closer to the graft sleeve proximal end than to the graft sleeve distal end, the support ring including (i) a helical coil having a helical coil first end and a helical coil second end, the helical coil defining a lumen and extending in an arc, wherein the helical coil first end and the helical coil second end are in an opposing relation to each other that defines a space between the helical coil first end and the helical coil second end, and is outside the lumen, the helical coil being fixed to the tubular wall at the fenestration, whereby the fenestration is within the are of the helical coil, and (ii) a wire extending through the lumen and having a wire first end and a wire second end, the wire traversing the space between the helical coil first end and the helical coil second end along at least one length of the wire between the wire first end and the wire second end, and wherein the wire first end and the wire second end are secured to each other.

In various embodiments, the wire includes nitinol.

In a further embodiment, the invention is a method of forming a support ring for an aortic prosthesis, comprising the steps of: (a) directing a wire through a lumen defined by a helical coil from a helical coil first end through a helical coil second end that is in opposition to the helical coil first end, and across a space defined by the helical coil first end and the helical coil second end that is outside the lumen, whereby the wire traverses the space between the helical coil first end and the helical coil second end along at least one length of the wire between a wire first end and a wire second end; and (b) securing the wire first end to the wire second end, thereby forming the support ring.

In various embodiments, the method further includes the step of fixing the support ring to a tubular graft having a tubular graft first end and a tubular graft second end, and a tubular wall extending between the tubular graft first end and the tubular graft second end, the tubular wall defining a fenestration, and wherein the fenestration is within the arc of the helical coil.

In still another embodiment, the invention is a method of forming an aortic prosthesis, comprising the steps of: (a) forming a tubular graft having a tubular graft first end and a tubular graft second end, and a tubular graft wall extending between the tubular graft first end and the tubular graft second end, the tubular graft wall defining a fenestration; (b) forming a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, and wherein the graft sleeve proximal end defines a plane that intersects a plane defined by the graft sleeve distal end; (c) fixing a support ring to the graft sleeve wall closer to the graft sleeve proximal end than to the graft sleeve distal end, thereby forming a graft sleeve assembly of the graft sleeve and the support ring; and (d) fixing the graft sleeve assembly to the tubular wall around the fenestration, thereby forming the aortic prosthesis.

In various embodiments, the method further includes the step of forming the support ring.

In various embodiments, the support ring is formed by the steps of: (a) directing a wire through a lumen defined by a helical coil extending in an arc from a helical coil first end through a helical coil second end in opposition to the helical coil first end, and across a space defined by the helical coil first end and the helical coil second end that is outside the lumen defined by the helical coil, whereby the wire traverses the space between the helical coil first end and the helical coil second end along at least one length of the wire between a wire first end and a wire second end; and (b) securing the wire first end to the wire second end, thereby forming the support ring.

In various embodiments, the method further includes the step of fixing the support ring to the tubular graft at the fenestration in the tubular wall, wherein the fenestration is within the arc of the helical coil, thereby forming the aortic prosthesis.

In another embodiment, the invention is a method of forming an aortic prosthesis, comprising the steps of: (a) forming a tubular graft having a tubular graft first end and a tubular graft second end, and a tubular wall extending between the tubular graft first end and the tubular graft second end, the tubular wall defining at least one fenestration between the tubular graft first end and the tubular graft second end; (b) forming a support ring by (i) directing a wire through a lumen defined by a helical coil from a helical coil first end through a helical coil second end that is in opposition to the helical coil first end, and across a space defined by the helical coil first end and the helical coil second end that is outside the lumen, whereby the wire traverses the space between the helical coil first end and the helical coil second end along at least one length of the wire between a wire first end and a wire second end; and (ii) securing the wire first end to the wire second end, thereby forming the support ring; and (c) fixing the support ring to the tubular graft at the fenestration in the tubular wall, wherein the fenestration is within the arc of the helical coil, thereby forming the aortic prosthesis.

A further embodiment of the invention is a method for implanting a branched aortic prosthesis, comprising the steps of: (a) directing an aortic prosthesis to an aortic surgical, site, the aortic prosthesis including, (i) a tubular graft component including a tubular graft first end and a tubular graft second end, and a tubular graft wall extending between the tubular graft first end and the tubular graft second end, the tubular graft wall defining at least one fenestration between the tubular graft first end and the tubular graft second end, (ii) a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, wherein the graft sleeve proximal end defines a plane that intersects a plane defined by the graft sleeve distal end, and wherein the graft sleeve wall is fixed to the tubular wall around the fenestration, and (iii) a support ring fixed to the graft sleeve wall, wherein the support ring is fixed to the graft sleeve wall closer to the graft sleeve proximal end than to the graft sleeve distal end; and (b) directing a branch stent graft distally through the graft sleeve until a branch stent graft proximal end is distal to the support ring, whereby the branch stent graft is secured by an interference fit between the branch stent graft distal end and the graft sleeve, thereby implanting the branched stent graft at the surgical site.

In various embodiments, the support ring includes: (a) a helical coil having a helical coil first end and a helical coil second end, the helical coil defining a lumen and extending in an are, wherein the helical coil first end and the helical coil second end are in an opposing relation to each other that defines a space between the helical coil first end and the helical coil second end and is outside the lumen, the helical coil being fixed to the tubular wall at the fenestration, wherein the fenestration is within the are of the helical coil; and (b) a wire extending through the lumen and having a wire first end and a wire second end, the wire traversing the space between the helical coil first end and the helical coil second end along at least one length of the wire between the wire first end and the wire second end, and wherein the wire first end and wire second end are secured to each other.

Stent grafts can be implanted at a surgical site that spans an aneurysm, in particular in the perivisceral segment of the aorta, by suitable methods, such as is known in the art. Following implantation, bridging stents can be delivered through the fenestration, fenestration ring and into a branch of the aorta, such a renal, superior mesenteric or celiac arteries. Suitable delivery devices for implanting stent grafts are described, for example, in U.S. Patent Application Nos: 63/111,357 and 63,153,701, and U.S. Ser. No. 210,381, the relevant teachings of all of which are hereby incorporated by reference in their entirety.

The relevant teachings of all patents, published applications and references cited herein are incorporated by reference in their entirety. The relevant teachings of U.S. Pat. Nos. U.S. Pat. Nos. 10,987,235, 11,000,359, 11,291,572, 11,278,390, 11,219,540, and 11,154,392; US Published Patent Application Nos.: US 2019/0269498 A1, US 2019/0231514 A1, US 2019/0231571 A1, US 2019/0247178 A1, US 2019/0269497 A1, US 2019/0282355 A1, US 2019/0321207 A1, US 2020/352700A1, and US 2021/0401602 A1; and U.S. application Ser. No. 17/522,251, are also incorporated by reference in their entirety. The relevant teachings of United States patent application, titled "Support Ring for Vascular Aortic Repair and Methods of Use," filed Jun. 13, 2022, by Eduardo Alejandro Garcia, Timothy Lostetter, and Eitan Magen International Application No. PCT/US22/33247) are also incorporated by reference in their entirety.

While example embodiments have been particularly shown and described, it will be understood by those in the art various changes in form and details may be made therein without departing from the scope of the embodiments encompassed by the appended claims.

What is claimed is:

1. A support ring for an aortic prosthesis, comprising a. a helical coil having a helical coil first end and a helical coil second end, the helical coil defining a lumen and extending in an arc, wherein the helical coil first end and the helical coil second end are in an opposing relation to each other that defines a space that is between the helical coil first end and the helical coil second end and is outside the lumen; and b. a wire extending through the lumen and having a wire first end and a wire second end, the wire traversing the space between the helical coil first end and the helical coil second end along at least one length of the wire between the wire first end and the wire second end, wherein the wire completes two or more complete loops and the wire first end and wire second end overlap with the first wire end radially spaced from the second wire end within the space between the helical coil first end and second end, and wherein the wire first end and the wire second end are secured to each other with a crimped connector, wherein a length of wire between the wire first end and the wire second end does not pass through the connector and lies in the traversed space.

2. The support ring of claim 1, wherein the crimped connector is in the space between the helical coil first end and the helical coil second end.

3. The support ring of claim 2, wherein the crimped connector includes at least one of tantalum, gold, platinum, iridium, nitinol, and stainless steel.

4. The support ring of claim 2, wherein the helical coil is radiopaque.

5. The support ring of claim 4, wherein the helical coil includes at least one of tantalum, gold, platinum, iridium, nitinol, tungsten, and stainless steel.

6. The support ring of claim 1, wherein the wire includes at least one of a shape-memory alloy and stainless steel.

7. The support ring of claim 6, wherein the wire includes a shape-memory alloy.

8. The support ring of claim 7, wherein the shape-memory alloy includes at least one of a nickel-titanium alloy, an iron-based alloy, a copper-based alloy, a zinc-based alloy, a gold-based alloy, and a high-temperature shape-memory alloy.

9. The support ring of claim 8, wherein the shape-memory alloy includes nitinol.

10. The support ring of claim 9, wherein the wire traverses the space between the helical coil first end and the helical coil second end at a plurality of lengths between the wire first end and the wire second end.

11. The support ring of claim 10, wherein the wire traverses the space between the helical coil first end and the helical coil second end at two, three, four, five, six, seven, eight, nine, or ten lengths along the wire.

12. The support ring of claim 11, further including a tubular graft having a tubular graft first end, a tubular graft second end, and a tubular graft wall extending between the tubular graft first end and tubular graft second end, the tubular graft wall defining at least one fenestration between the tubular graft first end and the tubular graft second end, wherein the helical coil is fixed to the tubular graft wall at the fenestration, and wherein the fenestration is within the arc of the helical coil.

13. The support ring of claim 12, wherein the tubular graft is a stent graft.

14. A branch sleeve assembly for an aortic prosthesis, comprising:

a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, and wherein the graft sleeve proximal end defines a plane that intersects a plane defined by the graft sleeve distal end; and a support ring fixed to the graft sleeve wall that is closer to the proximal end of the graft sleeve than to the graft sleeve distal end, wherein the support ring comprises a helical coil having a helical coil first end and a helical coil second end, the helical coil defining a lumen, wherein the helical coil first end and the helical coil second end are in an opposing relation to each other that defines a space therebetween and outside the lumen; and a wire extending through the lumen and having a wire first end and a wire second end, the wire traversing the space between the helical coil first end and the helical coil second end, wherein the wire completes two or more complete loops and the wire first end and wire second end overlap with the first wire end radially spaced from the second wire end within the space between the helical coil first end and second end, and wherein the wire first end and the wire second end are secured to each other with a crimped connector, wherein a length of wire between the wire first end and the wire second end does not pass through the connector and lies in the traversed space.

15. An aortic prosthesis, comprising:

a) a tubular graft component including a tubular graft component first end and a tubular graft component second end, and a tubular graft wall extending between the tubular graft component first end and the tubular graft component second end, the tubular graft wall defining at least one fenestration between the tubular graft component first end and the tubular graft component second end; and b) a support ring at the tubular wall, the support ring including a helical coil having a helical coil first end and a helical coil second end, the helical coil defining a lumen and extending in an arc, wherein the helical coil first end and the helical coil second end are in an opposing relation to each other that defines a space between the helical coil first end and the helical coil second end and is outside the lumen, the helical coil being fixed to the tubular wall at the fenestration, wherein the fenestration is within the arc of the helical coil, and a wire extending through the lumen and having a wire first end and a wire second end, the wire traversing the space between the wire first end and the wire second end along at least one length of the wire between the wire first end and the wire second end, wherein the wire completes two or more complete loops and the wire first end and wire second end overlap with the first wire end radially spaced from the second wire end within the space between the helical coil first end and second end, and wherein the wire first end and the wire second end are secured to each other with a crimped connector, wherein a length of wire between the wire first end and the wire second end does not pass through the connector and lies in the traversed space.

16. A method of forming a support ring for an aortic prosthesis, comprising the steps of:

a) directing a wire through a lumen defined by a helical coil from a helical coil first end through a helical coil second end that is in opposition to the helical coil first end, and across a space defined by the helical coil first end and the helical coil second end that is outside the lumen, whereby the wire completely traverses the space between the helical coil first end and the helical coil second end along at least two lengths of the wire between a wire first end and a wire second end, which overlap with the first wire end radially spaced from the second wire end within the space between the helical coil first end and second end; and b) securing the wire first end to the wire second end with a crimped connector, thereby forming the support ring, such that a length of wire between the wire first end and the wire second end does not pass through the connector and lies in the traversed space.

17. The method of claim 16, further including the step of fixing the support ring to a tubular graft having a tubular graft first end and a tubular graft second end, and a tubular wall extending between the tubular graft first end and the tubular graft second end, the tubular wall defining a fenestration, and wherein the fenestration is within the arc of the helical coil.

18. A method for implanting a branched aortic prosthesis, comprising the steps of:

directing an aortic prosthesis to an aortic surgical site, the aortic prosthesis including a tubular graft component including a tubular graft first end and a tubular graft second end, and a tubular graft wall extending between the tubular graft first end and the tubular graft second end, the tubular graft wall defining at least one fenestration between the tubular graft first end and the tubular graft second end, a graft sleeve having a graft sleeve proximal end, a graft sleeve distal end, and a graft sleeve wall extending between the graft sleeve proximal end and the graft sleeve distal end, the graft sleeve proximal end having a base diameter and the graft sleeve distal end having a diameter less than the base diameter, wherein the graft sleeve proximal end defines a plane that intersects a plane defined by the graft sleeve distal end, and wherein the graft sleeve wall is fixed to the tubular wall around the fenestration, and a support ring fixed to the graft sleeve wall, wherein the support ring is fixed to the graft sleeve wall closer to the graft sleeve proximal end than to the graft sleeve distal end; and wherein the support ring comprises a helical coil having a helical coil first end and a helical coil second end, the helical coil defining a lumen, wherein the helical coil first end and the helical coil second end are in an opposing relation to each other that defines a space therebetween and is outside the lumen; and a wire extending through the lumen and having a wire first end and a wire second end, the wire traversing the space between the helical coil first end and the helical coil second end, wherein the wire completes two or more complete loops and the wire first end and wire second end overlap with the first wire end radially spaced from the second wire end within the space between the helical coil first end and second end, and wherein the wire first end and the wire second end are secured to each other with a crimped connector, wherein a length of wire between the wire first end and the wire second end does not pass through the connector and lies in the traversed space;

directing a branch stent graft distally through the graft sleeve until a branch stent graft proximal end is distal to the support ring, whereby the branch stent graft is secured by an interference fit between the branch stent graft distal end and the graft sleeve, thereby implanting the branched stent graft at the surgical site.

* * * * *